United States Patent
Babish et al.

(10) Patent No.: US 8,193,201 B2
(45) Date of Patent: Jun. 5, 2012

(54) SYNERGISTIC ANTI-INFLAMMATORY PHARMACEUTICAL COMPOSITIONS AND RELATED METHODS USING CURCUMINOIDS OR METHYLXANTHINES

(75) Inventors: John G. Babish, Brooktondale, NY (US); Matthew L. Tripp, Gig Harbor, WA (US); Jeffrey S. Bland, Fox Island, WA (US)

(73) Assignee: Metaproteomics, LLC, San Clemente, CA (US)

( * ) Notice: Subject to any disclaimer, the term of this patent is extended or adjusted under 35 U.S.C. 154(b) by 0 days.

(21) Appl. No.: 13/073,388

(22) Filed: Mar. 28, 2011

(65) Prior Publication Data
US 2011/0172253 A1 Jul. 14, 2011

Related U.S. Application Data

(62) Division of application No. 10/789,817, filed on Feb. 27, 2004, now Pat. No. 7,914,831.

(51) Int. Cl.
*A01N 43/90* (2006.01)
*A01N 31/00* (2006.01)
*A61K 31/522* (2006.01)
*A61K 31/45* (2006.01)

(52) U.S. Cl. .................. 514/263.34; 514/729
(58) Field of Classification Search ............ 514/263.34, 514/729
See application file for complete search history.

(56) References Cited

U.S. PATENT DOCUMENTS

| | | | |
|---|---|---|---|
| 3,451,821 A | 6/1969 | Todd et al. |
| 3,536,495 A | 10/1970 | Westermann et al. |
| 3,552,975 A | 1/1971 | Worden |
| 3,720,517 A | 3/1973 | Bavisotto et al. |
| 3,932,603 A | 1/1976 | Haas |
| 3,933,919 A | 1/1976 | Wilkinson |
| 3,965,188 A | 6/1976 | Westermann et al. |
| 4,123,561 A | 10/1978 | Grant |
| 4,133,903 A | 1/1979 | Thiele et al. |
| 4,148,873 A | 4/1979 | Owades |
| 4,154,865 A | 5/1979 | Grant |
| 4,170,638 A | 10/1979 | Owades |
| 4,389,421 A | 6/1983 | Palamand |
| 4,401,684 A | 8/1983 | Versluys |
| 4,473,551 A | 9/1984 | Schinitsky |
| 4,554,170 A | 11/1985 | Panzer et al. |
| 4,590,296 A | 5/1986 | Cowles et al. |
| 4,644,084 A | 2/1987 | Cowles et al. |
| 4,692,280 A | 9/1987 | Spinelli |
| 4,758,445 A | 7/1988 | Klusters |
| 4,767,640 A | 8/1988 | Goldstein et al. |
| 4,857,554 A | 8/1989 | Kallimanis |
| 5,006,337 A | 4/1991 | Motitschke et al. |
| 5,013,571 A | 5/1991 | Hay |
| 5,041,300 A | 8/1991 | Todd et al. |
| 5,073,396 A | 12/1991 | Todd, Jr. |
| 5,082,975 A | 1/1992 | Todd, Jr. et al. |
| 5,155,276 A | 10/1992 | Paul |
| 5,166,449 A | 11/1992 | Todd, Jr. et al. |
| 5,264,236 A | 11/1993 | Ogasahara et al. |
| 5,286,506 A | 2/1994 | Millis et al. |
| 5,370,863 A | 12/1994 | Barney et al. |
| 5,387,425 A | 2/1995 | Hsu et al. |
| 5,604,263 A | 2/1997 | Tobe et al. |
| 5,641,517 A | 6/1997 | Eskeland et al. |
| 5,827,895 A | 10/1998 | Nutter et al. |
| 5,866,162 A | 2/1999 | Grattan |
| 5,919,813 A | 7/1999 | De Juan |
| 5,968,539 A | 10/1999 | Beerse et al. |
| 5,296,637 A | 2/2000 | Ting et al. |
| 6,020,019 A | 2/2000 | Ting et al. |
| 6,129,907 A | 10/2000 | Sreenivasan et al. |
| 6,200,594 B1 | 3/2001 | Ernest et al. |
| 6,210,701 B1 | 4/2001 | Darland et al. |
| 6,224,871 B1 | 5/2001 | Hastings et al. |
| 6,264,995 B1 | 7/2001 | Newmark et al. |
| 6,291,483 B1 | 9/2001 | Upadhyay et al. |
| 6,383,527 B1 | 5/2002 | Artman et al. |
| 6,391,346 B1 | 5/2002 | Newmark et al. |
| 6,440,465 B1 | 8/2002 | Meisner |
| 6,447,762 B1 | 9/2002 | Galcerá |
| 6,482,456 B1 | 11/2002 | Yokoo et al. |
| 6,492,429 B1 | 12/2002 | Graus et al. |
| 6,583,322 B1 | 6/2003 | Shahlai et al. |
| 6,689,388 B2 | 2/2004 | Kuhrts |
| 6,790,459 B1 | 9/2004 | Cheng et al. |
| 6,801,860 B1 | 10/2004 | Dessen et al. |
| 7,078,062 B2 | 7/2006 | Haas |
| 7,144,590 B2 | 12/2006 | Kuhrts |
| 7,195,785 B2 | 3/2007 | Babish et al. |

(Continued)

FOREIGN PATENT DOCUMENTS

CN 1203268 12/1998

(Continued)

OTHER PUBLICATIONS

Abel-salam et al., Pharmacological Research, England 47(4), pp. 311-340 (Apr. 2003).
Albal, MV., et al., "Clinical evaluation of berberine in mycotic infections." Indian J. Ophthalmol 34:91-2 (1986).
Anto, et al., "Anti-inflammatory Activity of Natural and Synthetic Curcuminoids", Pharmacy and Pharmacology Communications, 4(2), pp. 103-106 (1998).
Baldermann et al., J. Chromatography A 1192(1):191-3 (May 23, 2008) (Epub Apr. 8, 2008); abstract only (1 page).
Bolick D et al., Endocrinology 144(12), pp. 5227-5231 (Dec. 2003).
Brown, et al. J. Chem. Soc. 545 (1959).
Buhler et al., Antioxidant Activities of Flavanoids, 3 pages, Nov. 2000.

(Continued)

*Primary Examiner* — Sreeni Padmanabhan
*Assistant Examiner* — Kendra D Carter
(74) *Attorney, Agent, or Firm* — McDermott Will & Emery LLP

(57) ABSTRACT

The invention provides compositions containing a fraction isolated or derived from hops and a methylxanthine. The invention additionally provides compositions containing a fraction derived from hops and a curcuminoid. The invention also provides methods of using such compositions to reduce inflammation.

25 Claims, 16 Drawing Sheets

U.S. PATENT DOCUMENTS

| | | | |
|---|---|---|---|
| 7,205,151 | B2 | 4/2007 | Babish et al. |
| 7,270,835 | B2 | 9/2007 | Tripp et al. |
| 7,279,185 | B2 | 10/2007 | Babish et al. |
| 7,332,185 | B2 | 2/2008 | Babish et al. |
| 7,431,948 | B2 | 10/2008 | Tripp et al. |
| 2002/0028852 | A1 | 3/2002 | Ghai et al. |
| 2002/0076452 | A1 | 6/2002 | Babish et al. |
| 2002/0077299 | A1 | 6/2002 | Babish et al. |
| 2002/0086062 | A1 | 7/2002 | Kuhrts |
| 2002/0086070 | A1 | 7/2002 | Kuhrts |
| 2002/0156087 | A1 | 10/2002 | Nuss et al. |
| 2003/0003212 | A1 | 1/2003 | Chien et al. |
| 2003/0008021 | A1 | 1/2003 | Babish et al. |
| 2003/0035851 | A1 | 2/2003 | Chen |
| 2003/0077313 | A1 | 4/2003 | Schwartz et al. |
| 2003/0096027 | A1 | 5/2003 | Babish et al. |
| 2003/0113393 | A1 | 6/2003 | Babish et al. |
| 2003/0133958 | A1 | 7/2003 | Kuno et al. |
| 2003/0180402 | A1 | 9/2003 | Jia et al. |
| 2003/0228369 | A1 | 12/2003 | Kuhrts |
| 2004/0072900 | A1 | 4/2004 | Artman et al. |
| 2004/0086580 | A1 | 5/2004 | Tripp et al. |
| 2004/0115290 | A1 | 6/2004 | Tripp et al. |
| 2004/0137096 | A1 | 7/2004 | Kuhrts |
| 2004/0151792 | A1 | 8/2004 | Tripp et al. |
| 2004/0219240 | A1 | 11/2004 | Babish et al. |
| 2005/0042317 | A1 | 2/2005 | Babish et al. |
| 2005/0129791 | A1 | 6/2005 | Babish et al. |
| 2005/0191375 | A1 | 9/2005 | Babish et al. |
| 2005/0192356 | A1 | 9/2005 | Babish et al. |
| 2006/0074052 | A1 | 4/2006 | Eliaz |
| 2006/0127511 | A1 | 6/2006 | Tripp et al. |
| 2006/0127512 | A1 | 6/2006 | Tripp et al. |
| 2006/0127513 | A1 | 6/2006 | Tripp et al. |
| 2006/0127514 | A1 | 6/2006 | Tripp et al. |
| 2006/0127515 | A1 | 6/2006 | Tripp et al. |
| 2006/0127516 | A1 | 6/2006 | Tripp et al. |
| 2006/0127517 | A1 | 6/2006 | Tripp et al. |
| 2006/0193933 | A1 | 8/2006 | Tripp et al. |
| 2006/0233902 | A1 | 10/2006 | Yajima et al. |
| 2007/0003646 | A1 | 1/2007 | Kuhrts |
| 2007/0020352 | A1 | 1/2007 | Tripp et al. |
| 2007/0065456 | A1 | 3/2007 | Woods |
| 2007/0154576 | A1 | 7/2007 | Tripp et al. |
| 2007/0160692 | A1 | 7/2007 | Tripp et al. |
| 2007/0166418 | A1 | 7/2007 | Tripp et al. |
| 2007/0172532 | A1 | 7/2007 | Babish et al. |
| 2007/0184133 | A1 | 8/2007 | Tripp et al. |
| 2008/0127720 | A1 | 6/2008 | Pauli et al. |
| 2008/0248131 | A1 | 10/2008 | Tripp et al. |
| 2009/0118373 | A1 | 5/2009 | Tripp et al. |

FOREIGN PATENT DOCUMENTS

| | | |
|---|---|---|
| DE | 1901277 | 8/1970 |
| DE | 2212148 | 9/1972 |
| DE | 3931147 | 3/1991 |
| DE | 19841615 | 3/2000 |
| EP | 0229022 | 7/1987 |
| EP | 0606599 A1 | 7/1994 |
| EP | 1481671 | 12/2004 |
| EP | 1543834 | 6/2005 |
| GB | 2330076 | 4/1999 |
| JP | 52145509 | 12/1977 |
| JP | 59059623 | 4/1984 |
| JP | 363211219 | 9/1988 |
| JP | 04202138 | 7/1992 |
| JP | 6312924 | 11/1994 |
| JP | 07165583 | 6/1995 |
| JP | 07194351 | 8/1995 |
| JP | 8073369 | 3/1996 |
| JP | 08073369 | 3/1996 |
| JP | 9067245 | 3/1997 |
| JP | 09502202 | 3/1997 |
| JP | 410025247 | 1/1998 |
| JP | 10152428 | 6/1998 |
| JP | 10179129 | 7/1998 |
| JP | 11246399 | 9/1999 |
| JP | 11513037 | 11/1999 |
| JP | 11335231 | 12/1999 |
| JP | 2001161338 | 6/2001 |
| JP | 2002-12550 | 1/2002 |
| RU | 2045955 | 10/1995 |
| SU | 1247011 | 7/1986 |
| WO | WO 9507079 | 3/1995 |
| WO | WO 97/31630 | 9/1997 |
| WO | WO 9749405 | 12/1997 |
| WO | WO 99/44623 | 9/1999 |
| WO | WO 99/61038 | 12/1999 |
| WO | WO 00/68356 | 11/2000 |
| WO | WO 00/74696 | 12/2000 |
| WO | WO 02/02582 | 1/2002 |
| WO | WO 02/32234 | 4/2002 |
| WO | WO 03/000185 | 1/2003 |
| WO | WO 03/035007 | 5/2003 |
| WO | WO 03/068205 | 8/2003 |
| WO | WO 03/075943 | 9/2003 |
| WO | WO 03/082249 | 10/2003 |
| WO | WO 2004/037180 | 5/2004 |
| WO | WO 2004/062611 | 7/2004 |
| WO | WO 2005/084230 | 9/2005 |
| WO | WO 2006/053249 | 5/2006 |
| WO | WO 2006/062681 | 6/2006 |
| WO | WO 2007/021694 | 2/2007 |
| WO | WO 2007/067812 | 6/2007 |
| ZA | 200000857 | 8/2001 |

OTHER PUBLICATIONS

Byrne, et al. J. Chem. Soc. (C):2810 (1971).
Carroccio, et al. Clin. Chem. 49(6):861-867 (2003).
Carson, J. Am. Chem. Soc. 73:1850-1851 (1951).
Chandra, et al. Indian J. Medical Research 60(1):138-142 (1972).
Charlier, et al. Eur. J. Med. Chem. 38:645-659 (2003).
Chattopadhyay et al., Current Science, 87(1) (Jul. 10, 2004).
Chen Wei-Jen et al., Journal of Agricultural and Food Chemistry 52(1), pp. 55-64 (Jan. 1, 2004).
Chou et al. Eur. J. Biochem. 115:207-216 (1981).
Chou, et al. Adv enzyme regul 22:27-55 (1983).
Chou, et al. Eur. J. Biochem. 115:207-216 (1981).
Chou, et al. J. Biol. Chem. 252(18):6438-6442 (1977).
Chou, et al. J. Theor. Biol. 35:285-297 (1972).
Chou, J. Theor. Biol. 59:253-276 (1976).
Chou, et al., TIPS, pp. 450-454, Nov. 1983.
Cohen, Protein Kinases—the major drug targets of the twenty-first century? Nature Reviews, 1: 309-315 (2002).
Costa, et al. Digest. Liver Dis. 35:642-647 (2003).
Davies, WL. Abstract—Fertiliser, Feeding Stuffs and Farm Supplies J. 11:694 (1926).
De Keukeleire "Fundamentals of Beer and Hop Chemistry" Quimica Nova, 23(1) pp. 108-112 (2000).
Ding, et al. Biochem. Biophy. Res. Comm. 261:218-223 (1999).
Exercise as Treatment for Arthritis, Rheumatic and Immunologic Diseases, Cleveland Clinic, www.clevelandclinic.org, Mar. 14, 2000.
Foucault et al., J. Chromatography A 808(1-2):3-22 (May 29, 1998); abstract only (3 pages).
Friedman, et al. J Cutan Med. Surg. 6(5):449-459 (2002).
Gao et al., J. Food Sci. Nutr. vol. 9, pp. 240-244 (2004).
Gerhauser, Beer Constituents as Potential Cancer Chemopreventive Agents, EP Journal of Cancer 41; 1941-1954: (2005).
Germany, "The Absolutely German Drink," contents of beer, 2004, 5 pages.
Gilani, "Studies on Antihypertensive and Antispasmodic Activities of Methanol Extract of *Acacia nilotica* Pods", Phytotherapy Research 13: 665-669 (1999).
Goldstein, et al. Am. J. Gastroenterol. 96(4):1019-1027 (2001).
Halter, et al. Gut 49:443-453 (2001).
Hamberg, et al. J. Bio. Chem. 246(22):6713-6721 (1971).
Hariddradilepah 01, TKDL, Aug. 1, 1999, XP003024376, (3 pages).
Huang, et al. Cancer Res. 51:813-819 (1991).
Information on "Hops and Beer Flavours", IOB Technical Symposium, Apr. 2001, pp. 1-9.
Information on "Zyflamend and Zyflamend PM", downloaded from Internet Aug. 30, 2002.

International Search Report for PCT /US06/30920, Aug. 3, 2007, 3 pages.
Jafri et al., Pakistan Journal of Science, vol. 61, No. 4, pp. 220-222 (Dec. 2009).
Kaltner, Investigation of formation of Hops Aroma and technological Measures for Products of Hops—Aromatic Beers, Technical University of Munich, 7 pp. corresponding to Kaltner, D., Technische Universitat Munchen, (Nov. 30, 2000), pp. 1-193, plus Tabs. AH1-AH31.
Kanematsu, et al. J Bone Miner Res 12(11):1789-1796 (1997).
Konda, et al., Arthritis & Rheumatism 62(6): 1683-1692, (2010).
Kuo et al., Cancer Letter, 203:127-137 (2004).
Lamy Virginie et al., Apoptosis, an Int'l Journal on Programmed Cell Death,13(10), pp. 1232-1242 (Aug. 25, 2008).
Lamy Virginie et al., Carcinogenesis, 28(7), pp. 1575-1581 (Jul. 2007).
Lerman et al, FASEB Journal, Fed. of American Soc. for Experimental Biol., vol. 18, No. 4-5 (Jan. 1, 2004).
Lopes, Curr. Med Res Opin. 8(3):145-149 (1982).
Mannering et al., Food, Nutrition and Chemical Toxicity X(X), pp. 311-323 (Jan. 1, 1993).
Meling, et al. Scand. J. Gastroenterol. 31:339-344 (1996).
Minich et al., Journal of nutrition and Metabolism, vol. 2010, article ID 467316, pp-1-11, (2010).
Murvadyaghrtam, TKDL, Jan. 1, 2001, XP003024377 (4 pages).
Murvadyaghrtam, TKDL, Jan. 1, 1990, XP003024379 (4 pages).
Newark, et al., "Beyond Aspirin", pp. 147-151, Hohm Press (2000).
Noreen, et al. J. Nat. Prod 61:2-7 (1998).
Office Action issued for U.S. Appl. No. 11/667,614 mailed Apr. 16, 2010.
Office Action issued for U.S. Appl. No. 11/667,615 mailed Mar. 16, 2010.
Office Action issued for U.S. Appl. No. 11/701,583 mailed Feb. 8, 2008.
Office Action issued for U.S. Appl. No. 11/701,583 mailed Jul. 6, 2009.
Office Action issued for U.S. Appl. No. 11/701,583 mailed Nov. 26, 2008.
Office Action issued in U.S. Appl. No. 10/464,834 on Aug. 3, 2010.
Office Action issued in U.S. Appl. No. 10/532,388 on Mar. 26, 2010.
Office Action issued in U.S. Appl. No. 10/590,301 on Aug. 19, 2010.
Office Action issued in U.S. Appl. No. 10/590,424 on Jun. 29, 2010.
Office Action issued in U.S. Appl. No. 10/789,814 on Jun. 11, 2010.
Office Action issued in U.S. Appl. No. 10/789,814 on Mar. 18, 2011.
Office Action issued in U.S. Appl. No. 11/344,555 on Jan. 19, 2011.
Office Action issued in U.S. Appl. No. 11/344,556 on Sep. 3, 2010.
Office Action issued in U.S. Appl. No. 11/344,556 on Dec. 16, 2009.
Office Action issued in U.S. Appl. No. 11/344,556 on Mar. 27, 2009.
Office Action issued in U.S. Appl. No. 11/344,557 on Mar. 25, 2010.
Office Action issued in U.S. Appl. No. 11/344,557 on Apr. 21, 2008.
Office Action issued in U.S. Appl. No. 11/344,557 on Aug. 28, 2009.
Office Action issued in U.S. Appl. No. 11/344,557 on Jan. 10, 2007.
Office Action issued in U.S. Appl. No. 11/344,557 on Sep. 26, 2007.
Office Action issued in U.S. Appl. No. 11/636,867 on Aug. 30, 2010.
Office Action issued in U.S. Appl. No. 11/636,867 on Mar. 8, 2011.
Office Action issued in U.S. Appl. No. 11/649,584 on Mar. 3, 2010.
Office Action issued in U.S. Appl. No. 11/344,552 on Sep. 8, 2010.
Office Action issued in U.S. Appl. No. 11/501,393 on Aug. 25, 2010.
Office Action issued in U.S. Appl. No. 11/729,696 on Nov. 1, 2010.
Office Action issued in U.S. Appl. No. 11/820,600 on Sep. 30, 2010.
Office Action issued in U.S. Appl. No. 11/820,607 on Oct. 12, 2010.
Office Action issued in U.S. Appl. No. 12/030,335 on Oct. 21, 2010.
Office Action issued in U.S. Appl. No. 12/048,613 on Dec. 8, 2010.
Office Action issued in U.S. Appl. No. 12/754,820 on Mar. 15, 2011.
Office Action issued in U.S. Appl. No. 12/626,392 on Oct. 27, 2010.
Office Action issued in U.S. Appl. No. 11/729,696 on Mar. 25, 2010.
Parts per Milliion, 1 page, 2004.
Pippa, et al. Scand. J. Gastroenterol. Suppl. 167:32-35 (1989).
Plewig, et al. J Invest. Dermatol. 65(6):532-536 (1975).
Poullis ,et al. J. Gastroenterol. Hepatol. 18:756-762 (2003).
Provital Group, Rosemary-eco Botany, 2007, 9 pages.
Q & A, (what does ppm or ppb mean?) 3 pages, 2004.
Rahman, M.M., et al., "Conjugated linoleic acid inhibits osteoclast differentiation of RAW264.7 cells by modulating RANKL signaling" J. Lipid Res., 47(8): 1739-1748, (2006).
Ringbom, et al. J. Nat Prod 61:1212-1215 (1998).
Røseth, Digest. Liver Dis. 35:607-609 (2003).
Schjerven, et al. Br. J. Dermatol. 149:484-491 (2003).
Schmalreck et al, Canadian Journal of Microbiology, vol. 21:205-212 (1975).
Shah, et al. Gut 48:339-346 (2001).
Shimamura, et al. Biochem. Biophys. Res. Comm. 289:220-224 (2001).
Shureiqi, et al. Cancer Res. 61:6307-6312 (2001).
Sivri, Fundam. Clinic. Pharmacol. 18:23-31 (2004).
Smith, et al., Natural Foam Stabilizing and Bittering Compounds Derived From Hops, Journal of the American Society of Brewing Chemists, vol. 56, No. 2, 1998, pp. 52-57.
Stephan T E et al., Biochemical Pharmacology, 55(4), pp. 505-514, (Feb. 15, 1998).
Stevens, Xanthohumol and related Prenylflavonoids from Hops and Beer: To Your Good Health, Science Direct, 2pp (2004).
Subbaramaiah, et al. Cancer Res. 60:2399-2404 (2000).
Suh, et al. Cancer Res 58:717-723 (1988).
Supplementary Partial European Search Report for related European Patent Application No. 05723895.8, 5 pages (2007).
Tagashira M et al., Bioscience, Biotechnology, and Biochemistry, 59(4), pp. 740-742 (Apr. 1995).
The national. 3 pages (1999).
Tibble, et al. Drugs Today 37(2):85-96 (2001).
Tibble, et al. Gut 45:362-366 (1999).
Tiktakaghrtam, TKDL, Jan. 1, 1922, XP003024378 (1922).
Tobe, et al. Biosci. Biotech. Biochem 61(1):158-159 (1997).
Turmeric: The Ayurvedic Spice of Life, published at www.bioponic.com/pdfs/TurmericAyurveda.pdf (2003).
US News and world report re Palliative Care, 10 pages (2008).
Van Montfrans et al. Inflammatory Signal Transduction in Crohn's Disease and Novel Therapeutic Approaches. Science Direct, Jun. 2, 2002, 20 pages. Biochemical Pharmacology, vol. 64, issues 5-6.
Vanhoenacker, et al., Journal of Chromatography, vol. 1035, No. 1, (Apr. 30, 2004), pp. 53-61.
Verzele, et al. Chemistry and analysis of hop and beer bitter acids, Developments in food science, 27, pp. 44-51, 88-139 (1991).
Verzele and De Keukeleire (eds.) Chemistry and Analysis of Hop and Beer Bitter Acids; Elsevier, Chapters 5, 20 pages (1991).
Verzele and De Keukeleire (eds.) Chemistry and Analysis of Hop and Beer Bitter Acids; Elsevier, Chapters 6, 8 pages (1991).
Wang, et al. Free Radical Biology & Medicine 27:612-616 (1999).
Ward, et al., Therapeutic Potential of Phosphoinositide 3-Kinase Inhibitors, Chemistry & Biology, vol. 10, 207-210, Mar. 2003.
Warner, et al. Proc Natl Acad Sci USA 96:7563-7568 (1999).
Yamamoto, et al. Abstract—Prostaglandins & Other Lipid Mediators 59:1-235 (1999).
Yamamoto, FEBS Letters 465:103-106 (2000).
Yui, et al. Biol. Pharm. Bull. 26(6):753-760 (2003).
Zhao Feng et al., Biological and Pharmaceutical Bulletin, 26(1), pp. 61-65 (Jan. 2003).
Pairet, et al. Inflamm. Res 47, Supplement 2S93-S101 (1998).
Ohkura et al., Japanese Joural of Pharmacognosy, 44(3):171-175, (1990).

[A] 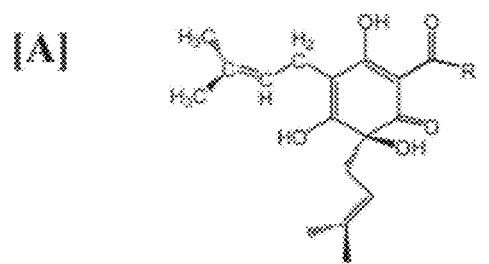
[B] 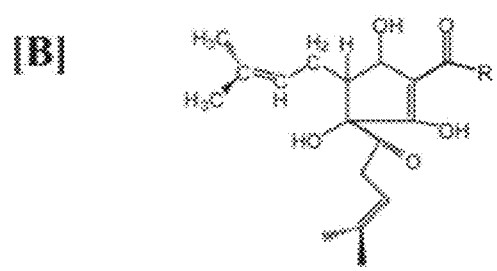
[C] 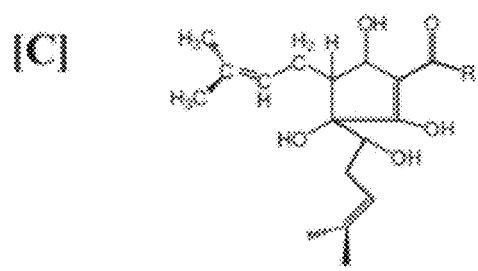
[D] 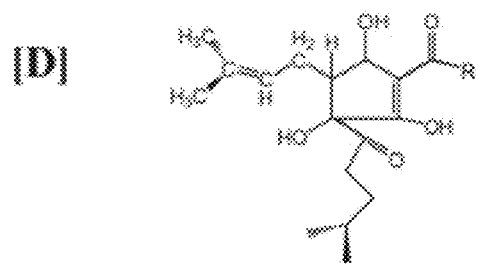
[E] 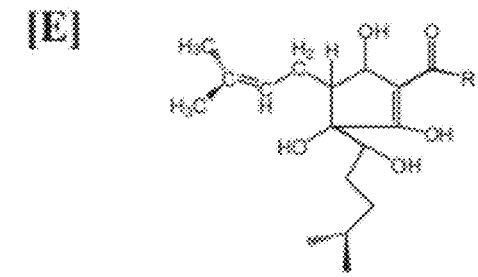
Figure 3

A
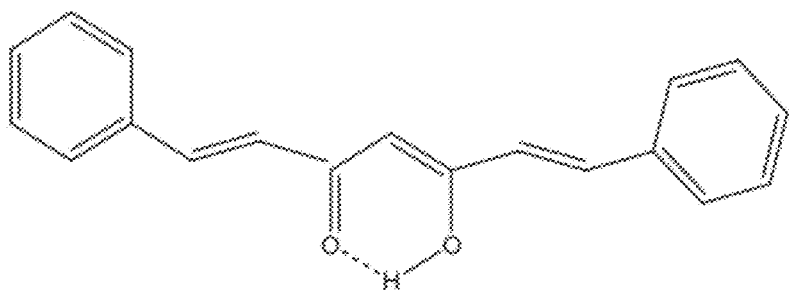
B
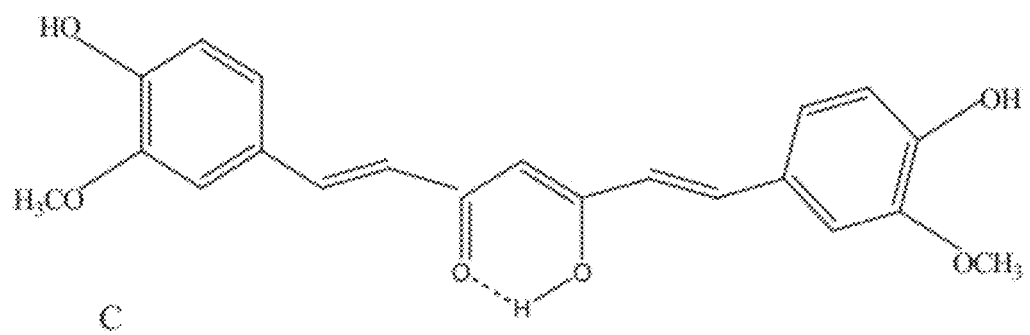
C
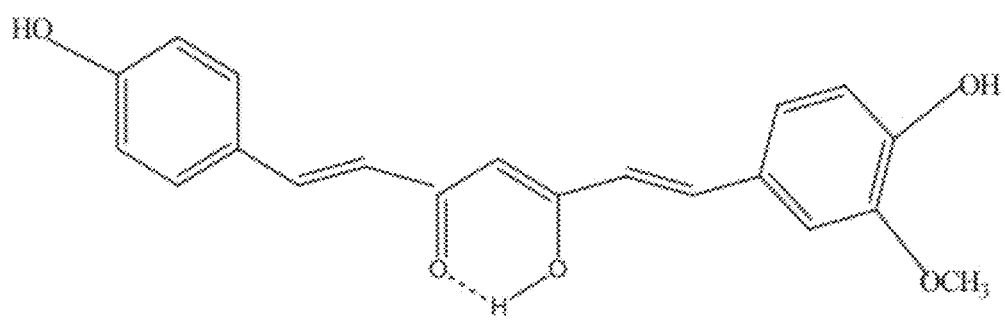
Figures 4 A-C

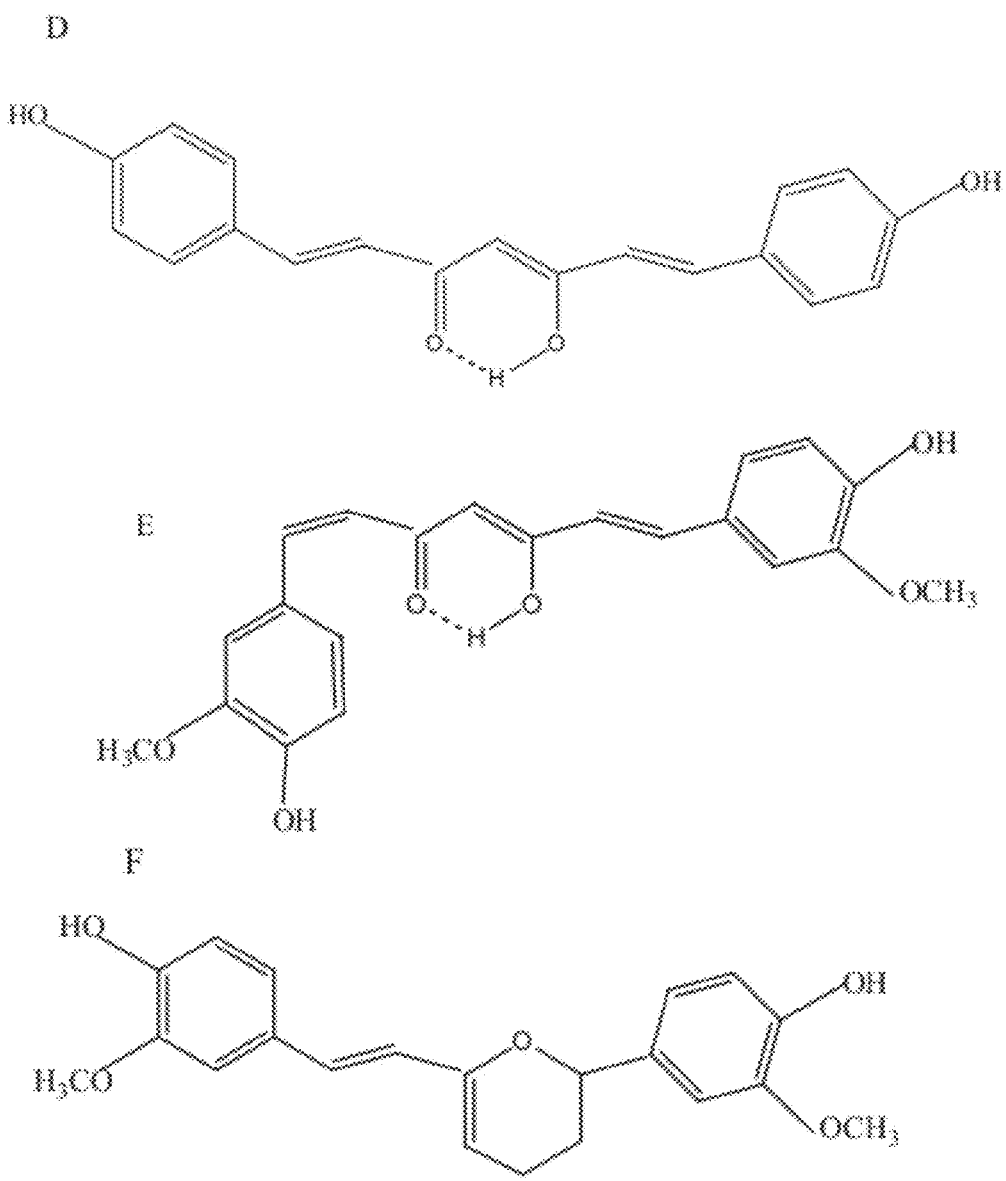
Figures 4 D-F

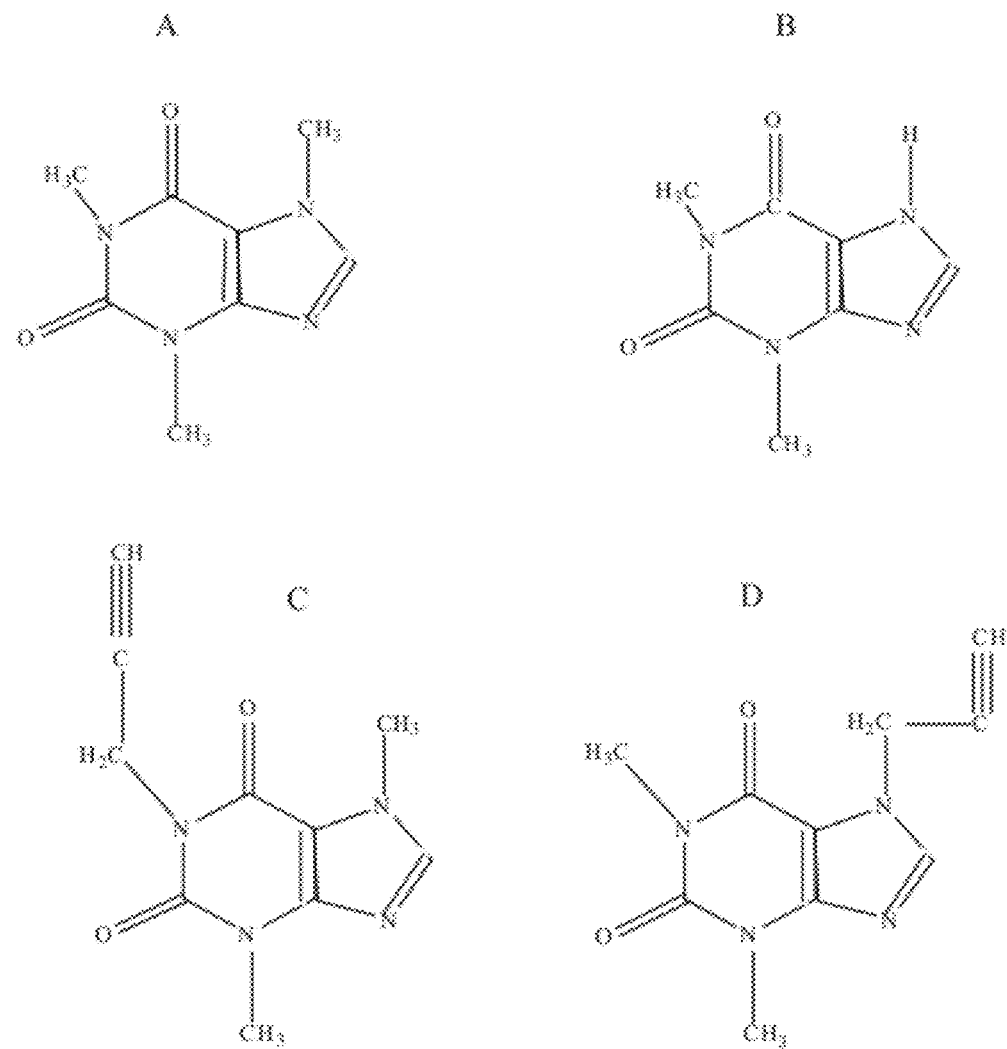
Figures 5 A-D

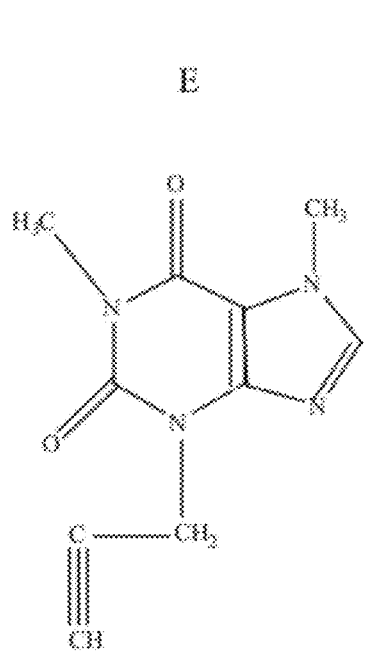
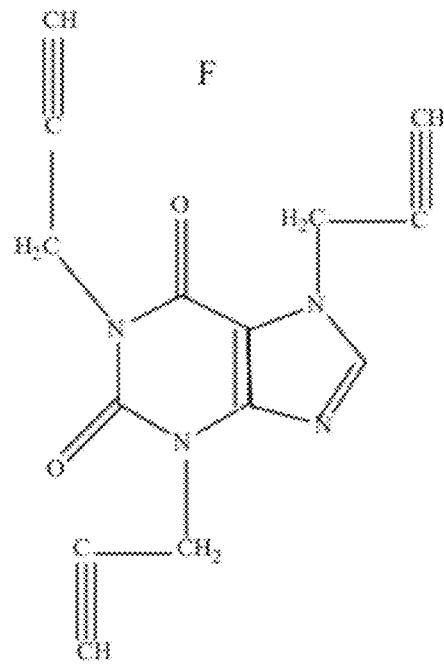
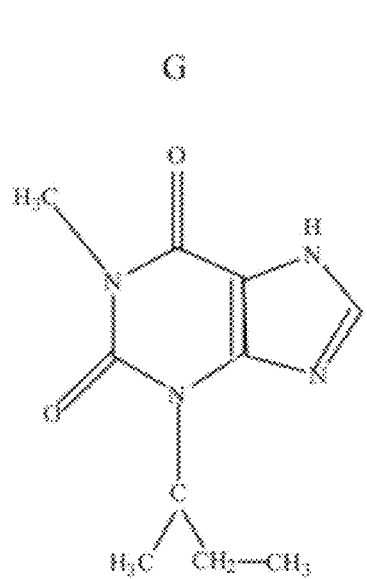
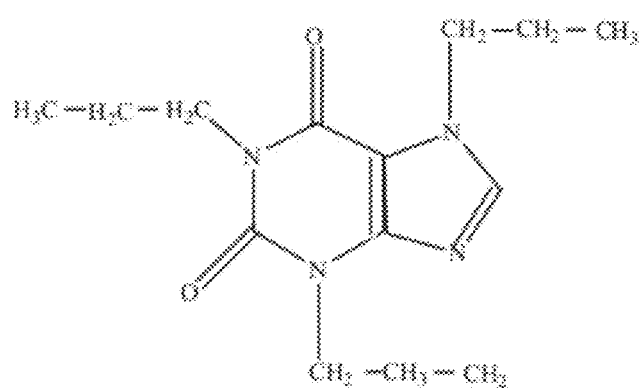
Figures 5 E-H

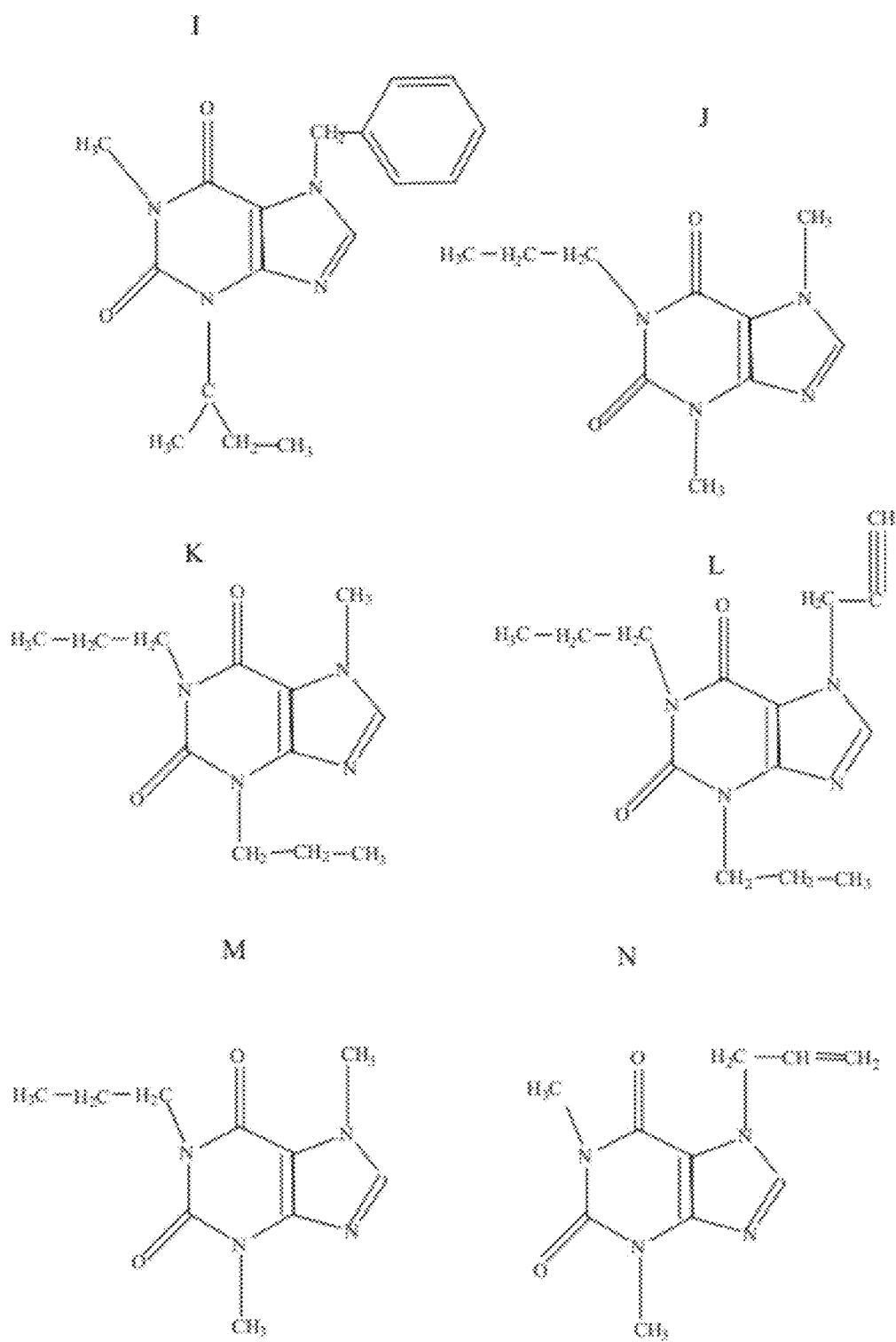
Figures 5I-N

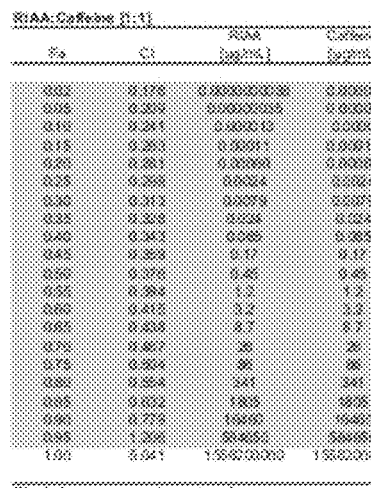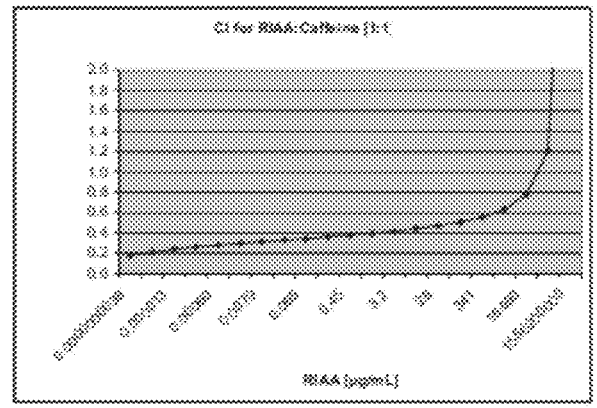
Figure 7E
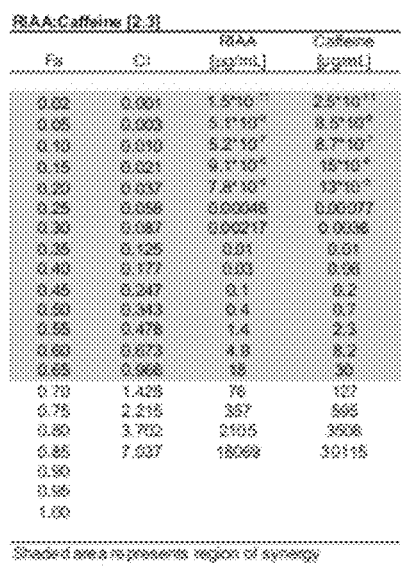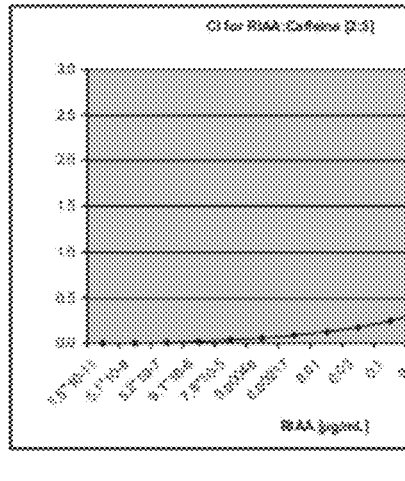
Figure 7F

SYNERGISTIC ANTI-INFLAMMATORY PHARMACEUTICAL COMPOSITIONS AND RELATED METHODS USING CURCUMINOIDS OR METHYLXANTHINES

CROSS-REFERENCE TO RELATED APPLICATION

This patent application is a Divisional of U.S. application Ser. No. 10/789,817, filed Feb. 27, 2004, now U.S. Pat. No. 7,914,831, which is expressly incorporated herein by reference.

BACKGROUND OF THE INVENTION

This invention relates to synergistic pharmaceutical compositions containing hops (*Humulus lupulus*) extracts or derivatives thereof in combination with curcuminoids or methylxanthines. The present invention also relates to methods of using compositions to reduce inflammation.

Prostaglandins (PGs) are ubiquitous hormones that function as both paracrine and autocrine mediators to affect a myriad of physiological changes in the immediate cellular environment. The varied physiological effects of PGs include inflammatory reactions such as rheumatoid arthritis and osteoarthritis, blood pressure control, platelet aggregation, induction of labor and aggravation of pain and fever. The discovery 30 years ago that aspirin and other non-steroidal analgesics inhibited PG production identified PG synthesis as a target for drug development. There are at least 16 different PGs in nine different chemical classes, designated. PGA to PGI. PGs are part of a larger family of 20-carbon-containing compounds called eicosanoids; they include prostacyclins, thromboxanes, and leukotrienes. The array of PGs produced varies depending on the downstream enzymatic machinery present in a particular cell type. For example, endothelial cells produce primarily $PGI_2$, whereas platelets mainly produce $TXA_2$.

Arachidonic acid serves as the primary substrate for the biosynthesis of all PGs. Cyclooxygenase (prostaglandin endoperoxide synthase, EC 1.14.991, COX) catalyzes the rate-limiting step in the metabolism of arachidonic acid to prostaglandin $H_2$ ($PGH_2$), which is further metabolized to various prostaglandins, prostacyclin and thromboxane A2 (see FIG. 1). In the early 1990s, it was established that COX exists in two isoforms, commonly referred to as COX-1 and COX-2. it was subsequently determined that the COX-1 and COX-2 proteins are derived from distinct genes that diverged well before birds and mammals. PGs generated via the COX-1 and COX-2 pathways are identical molecules and therefore have identical biological effects. COX-1 and COX-2, however, may generate a unique pattern and variable amounts of eicosanoids; therefore, relative differences in the activation of these isozymes may result in quite dissimilar biological responses. Differences in the tissue distribution and regulation of COX-1 and COX-2 are now considered crucial for the beneficial as well as adverse effects of COX inhibitors.

The generally held concept (COX dogma) is that COX-1 is expressed constitutively in most tissues whereas COX-2 is the inducible enzyme triggered by pro-inflammatory stimuli including mitogens, cytokines and bacterial lipopolysaccharide (LPS) in cells in vitro and in inflamed sites in vivo. Based primarily on such differences in expression, COX-1 has been characterized as a housekeeping enzyme and is thought to be involved in maintaining physiological functions such as cytoprotection of the gastric mucosa, regulation of renal blood flow, and control of platelet aggregation. COX-2 is considered to mainly mediate inflammation, although constitutive expression is found in brain, kidney and the gastrointestinal tract.

Prostaglandins (PG) are believed to play an important role in maintenance of human gastric mucosal homeostasis. Current dogma is that COX-1 is responsible for PG synthesis in normal gastric mucosa in order to maintain mucosal homeostasis and that COX-2 is expressed by normal gastric mucosa at low levels, with induction of expression during ulcer healing, following endotoxin exposure or cytokine stimulation. It now appears that both COX-1 and COX-2 have important physiological roles in the normal gastric mucosa.

Compounds that inhibit the production of PGs by COX have become important drugs in the control of pain and inflammation. Collectively these agents are known as non-steroidal anti-inflammatory drugs (NSAIDs) with their main indications being osteoarthritis and rheumatoid arthritis. However, the use of NSAIDs, and in particular aspirin, has been extended to prophylaxis of cardiovascular disease. Over the last decade, considerable effort has been devoted to developing new molecules that are direct inhibitors of the enzymatic activity of COX-2, with the inference that these compounds would be less irritating to the stomach with chronic use.

The major problem associated with ascertaining COX-2 selectivity (i.e. low gastric irritancy) is that differences in assay methodology can have profound effects on the results obtained. Depicted in Table 1 are the categories of the numerous in vitro assays that have been developed for testing and comparing the relative inhibitory activities of NSAID and natural compounds against COX-1 and COX-2. These test systems can be classified into three groups: (1) systems using animal enzymes, animal cells or cell lines, (2) assays using human cell lines, or human platelets and monocytes, and (3) currently evolving models using human cells that are representative of the target cells for the anti-inflammatory and adverse effects NSAID and dietary supplements. Generally, models using human cell lines or human platelets and monocytes are the current standard and validated target cell models have not been forthcoming. A human gastric cell line capable of assessing potential for gastric irritancy is a critical need.

The enzymes used can be of animal or human origin, they can be native or recombinant, and they can be used either as purified enzymes, in microsomal preparations, or in whole-cell assays. Other system variables include the source of arachidonic acid. PG synthesis can be measured from endogenously released arachidonic acid or exogenously added arachidonic acid. In the later case, different concentrations are used in different laboratories.

An ideal assay for COX-2 selectivity would have the following characteristics: (1) whole cells should be used that contain native human enzymes under normal physiological control regarding expression; (2) the cells should also be target cells for the anti-inflammatory and adverse effects of the compounds; (3) COX-2 should be induced, thereby simulating an inflammatory process, rather than being constitutively expressed; and (4) PG synthesis should be measured from arachidonic acid released from endogenous stores rather than from exogenously added arachidonic acid.

TABLE 1

Classification of test systems for in vitro assays assessing
COX-2 selectivity of anti-inflammatory compounds†

| I. TEST SYSTEMS | | |
|---|---|---|
| A. ANIMAL | B. HUMAN | C. TARGET |
| Enzymes | Enzymes | Human Gastric Mucosa Cells |
| Cells | Cells | Human Chondrocytes |
| Cell lines | Cell lines | Human Synoviocytes |

| D. OTHER SYSTEM VARIABLES | |
|---|---|
| 1. | Source of arachidonic acid-endogenous or exogenous; |
| 2. | Various expression systems for gene replication of COX-1 and COX-2; |
| 3. | The presence or absence of a COX-2 inducing agent; |
| 4. | COX-2 inducing agents are administered at different concentrations and for different periods of time; |
| 5. | Duration of incubation with the drug or with arachidonic acid; |
| 6. | Variation in the protein concentration in the medium. |

†Adapted from Pairet, M. and van Ryn, J. *Inflamm. Res.* 47, Supplement:2S93-S101 (1998) and incorporated herein by reference.

No laboratory has yet developed an ideal assay for COX-2 selectivity. The whole cell system most commonly used for prescription (Rx) and over the counter (OTC) products is the human whole blood assay developed by the William Harvey Institute (Warner et al., *Proc Natl Acad Sci USA* 96:7563-7568 (1999)). To date, this assay format has developed more data supporting clinical relevance than any other. However, new research on the role of constitutive expression of COX-2 in normal gastric mucosa necessitates revisiting the relevance of the use of platelets to model COX-1 inhibition in the absence of COX-2. The extrapolation of gastrotoxicity from platelet studies is no longer on a sound molecular basis. The validation of a human gastric mucosal cell line for establishing the potential target tissue toxicity of cyclooxygenase inhibitors represents a critical need for the development of safe and effective anti-inflammatory agents.

An ideal formulation for the treatment of inflammation would inhibit the induction and activity of COX-2 without inhibiting the synthesis of $PGE_2$ in gastric mucosal cells. However, conventional non-steroidal anti-inflammatory drugs lack the specificity of inhibiting COX-2 without affecting gastric $PGE_2$ synthesis and are at risk to cause damages on the gastrointestinal system, when used for extended periods. Indeed, even the newly developed, anti-inflammatory drugs such as rofecoxib (Vioxx®, Merck & Co., Inc.) and celecoxib (Celebrex®, Pfizer, Inc.) produce untoward gastric toxicity in the form of induced spontaneous bleeding and delay of gastric ulcer healing.

NSAID Toxicity

NSAIDs are known to cause serious health problems including gastric bleeding and kidney damage. In the United States, there are over 13 million regular users of NSAIDs, 70 million NSAID prescriptions written every year, and 30 billion over the counter NSAIDs tablets sold annually. NSAID-induced disease causes 103,000 hospitalizations per year and an estimated 16,500 deaths annually. Twenty percent of all chronic NSAID users will develop a peptic ulcer. NSAID users have a greater risk—three to four times higher—to upper gastrointestinal bleeding, perforation, or both. Eighty-one percent of patients hospitalized with serious NSAID-induced complications had no previous gastrointestinal symptoms. People over 60 years of age have a significantly higher probability of experiencing complications associated with NSAID use. Moreover, 21% of all adverse drug reaction in the United States are due to NSAID use.

The new selective COX-2 inhibitors such as celecoxib and rofecoxib have been shown to offer a safer alternative to most NSAIDs. However recent studies indicate that selective COX-2 inhibitors do not completely eliminate gastrointestinal toxicity. In fact in cases of inflammation or ulceration of the gastrointestinal tract, prescription COX-2 inhibitors may delay ulcer healing.

Thus, it would be useful to identify a natural formulation of compounds that would specifically inhibit or prevent the synthesis of prostaglandins by COX-2 with little or no effect on synthesis of $PGE_2$ in the gastric mucosa. Such a formulation would be useful for preserving the health of joint tissues, for treating arthritis or other inflammatory conditions. The term "specific or selective COX-2 inhibitor" was coined to embrace compounds or mixtures of compounds that selectively inhibit COX-2 over COX-1. However, while the implication is that such a calculated selectivity wilt result in lower gastric irritancy, unless the test materials are evaluated in gastric cells, the term "selective COX-2 inhibitor" does not carry assurance of safety to gastrointestinal cells. Only testing of compound action in target tissues, inflammatory cells and gastric mucosal cells will identify those agents with low potential for stomach irritation.

Therefore, it would be useful to identify a composition that would specifically inhibit or prevent the expression of COX-2 enzymatic activity in inflammatory cells, while having little or no effect on $PGE_2$ synthesis in gastric mucosal cells so that these formulations could be used with no gastrointestinal upset. Furthermore, such formulations should allow for healing of pre-existing ulcerative conditions in the stomach. The present invention satisfies this need and provides related advantages as well.

SUMMARY OF THE INVENTION

The invention provides compositions containing a fraction isolated or derived from hops and a methylxanthine. The invention additionally provides compositions containing a fraction derived from hops and a curcuminoid. The invention also provides methods of using such compositions to reduce inflammation.

BRIEF DESCRIPTION OF THE DRAWINGS

FIG. 3 illustrates exemplary fractions isolated or derived from hops. FIG. 3A shows the alpha-acid genus (AA) and representative species humulone (R=—$CH_2CH(CH_3)_2$), cohumulone (R=, —$CH(CH_3)_2$), and adhumulone (R=—$CH(CH_3)CH_2CH_3$); FIG. 3B shows the isoalpha acid genus (IAA) and representative species isohumulone (R=—$CH_2CH(CH_3)_2$), isocohumulone (R=, —$CH(CH_3)_2$), and isoadhumulone (R=—$CH(CH_3)CH_2CH_3$); FIG. 3C shows the reduced isomerized isoalpha acid genus (RIAA) and representative species dihydro-isohumulone (R=—$CH_2CH(CH_3)_2$) dihydro-isocohumulone (R=, —$CH(CH_3)_2$), and dihydro-isoadhumulone (R=, —$CH(CH_3)CH_2CH_3$); FIG. 3D shows the tetra-hydroisoalpha acid genus (THIAA) and representative species tetra-hydro-isoadhumulone (R=, —CH$_2$CH(CH$_3$)$_2$), tetra-hydro-isocohumulone ((R═, —CH (CH$_3$)$_2$), and tetra-hydro-isoadhumulone (R═—CH(CH$_3$) CH$_2$CH$_3$); FIG. 3E shows and the hexa-hydroisoalpha acid (HHIAA) genus with representative species hexa-hydro-isohumulone (R═—CH$_2$CH(CH$_3$)$_2$) hexa-hydro-isocohumulone (R═, —CH(CH$_3$)$_2$), and hexa-hydro-isoadhumulone (R═—CH(CH$_3$)CH$_2$CH$_3$).

FIGS. 4A-F illustrate the general chemical structure of the curcuminoid genus (A) and exemplary curcuminoids: curcumin (B), demethoxycurcumin (C), bisdemethoxycurcumin (D), the cis-trans geometrical isomer of curcumin (E), and cyclocurcumin (F).

FIGS. 5A-N show the structures of exemplary methylxanthines: caffeine (A); theophylline (B); 1-proparagyl 3,7-dimethyl xanthine (C); 7-proparagyl 1,3-dimethyl xanthine (D); 3-proparagyl 1,7-dimethyl xanthine (E); 1,3,7-triproparagyl xanthine (F); 3-isobutyl-1-methylxanthine (IBMX)(G); 1,3,7-tripropyl xanthine (H); 7-benzyl-IBMX (I); 1-propyl 3,7-dimethyl xanthine (J); 1,3-dipropyl 7-methyl xanthine (K); 1,3-dipropyl 7-proparagyl xanthine (L); 3,7-dimethyl 1-propyl xanthine (M); and 7-allyl 1,3-dimethyl xanthine (N).

DETAILED DESCRIPTION OF THE INVENTION

Figure 1:
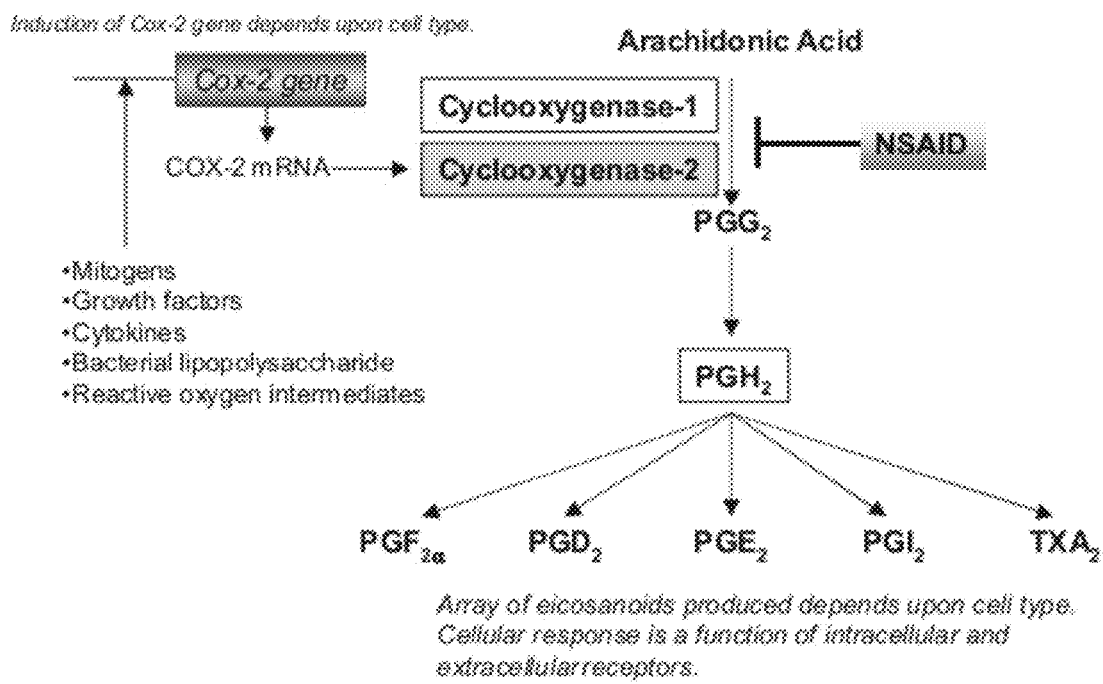
FIG. 1 depicts the induction of cyclooxygenase-2 and the metabolism of arachidonic acid to prostaglandins and other eicosanoids by the cyclooxygenase enzymes. The action of non-steroidal anti-inflammatory agents is through direct inhibition of the cyclooxygenase enzymes.
Figure 2:
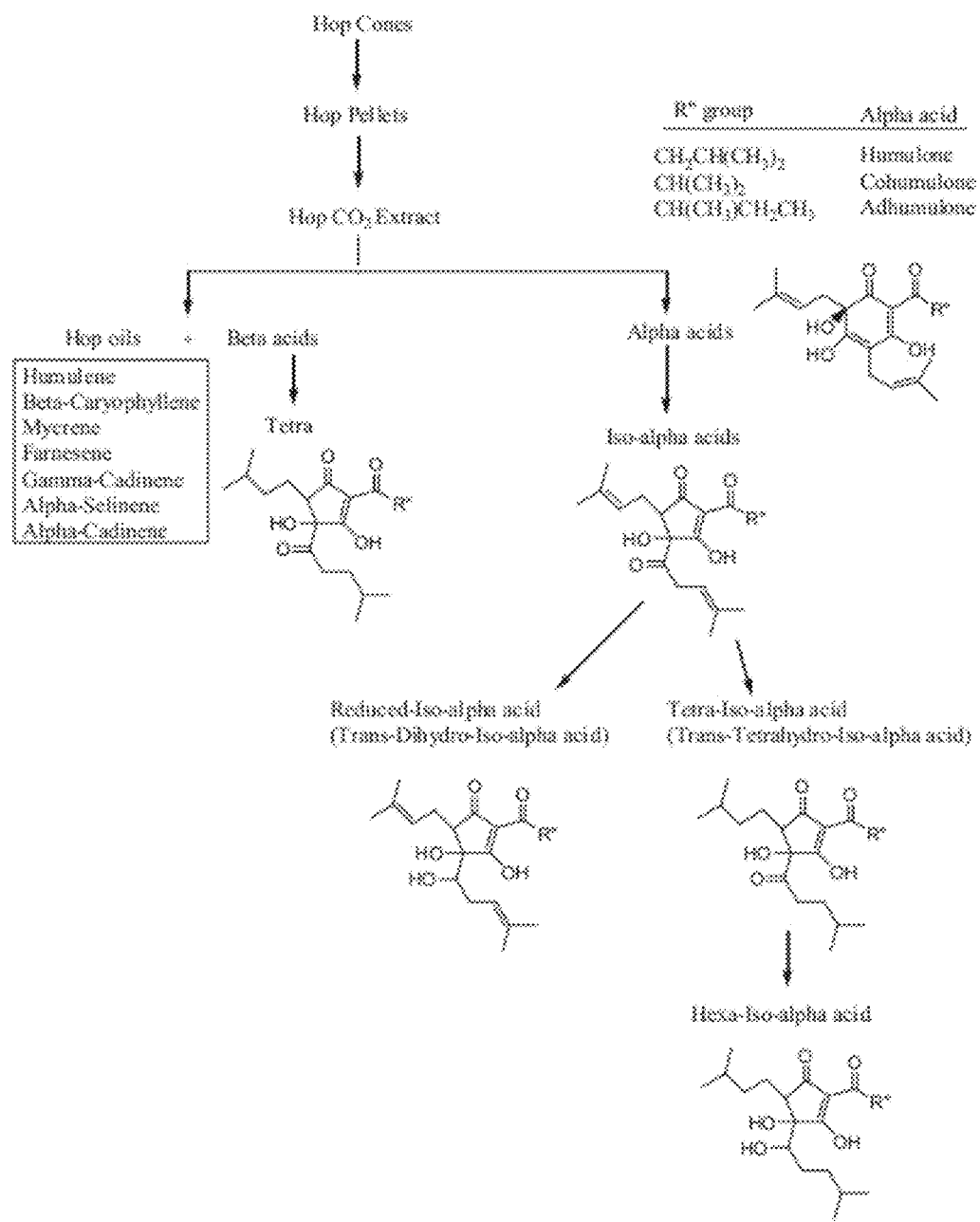
FIG. 2 shows an outline of fractions and compounds that can be obtained from hops.

The present invention provides compositions and methods for reducing inflammation, in particular, the invention provides a fraction isolated or derived from hops (*Humulus lupulus*) in combination with a curcuminoid or a methylxanthine such as caffeine. The invention provides hops (*Humulus lupulus*) extracts or derivatives thereof in combination with a curcuminoid or methylxanthine for use in treating inflammation in a patient prophylactically and/or therapeutically.

The invention also provide methods of reducing inflammation by administering a fraction isolated or derived from hops such as an isoalpha acid or reduced isoalpha acid in combination with curcumin, which synergistically inhibits prostaglandin E$_2$ (PGE$_2$). The invention additionally provides methods of reducing inflammation by administering a fraction isolated or derived from hops such as an isoalpha acid or reduced isoalpha acid in combination with a methylxanthine, which synergistically inhibits PGE$_2$.

The acute toxicity of hops derivatives is very low. Therefore, relatively high doses of hops derivatives can be used, if desired, without toxic effects due to the hops. Toxic doses are considerably higher than the therapeutic doses contemplated in accordance with the present invention.

The invention also provides a pharmaceutical composition comprising an active amount of hops extracts or derivatives thereof, in combination with a curcuminoid or methylxanthine. The invention further provides for use of hops extracts or derivatives thereof, significantly reducing and/or therapeutically treating an inflammatory disorder.

As used herein, the term "dietary supplement" refers to compositions consumed to affect structural or functional changes in physiology. The term "therapeutic composition" refers to compounds administered to treat or prevent a disease or to ameliorate a sign or symptom associated with a disease.

As used herein, the term "effective amount" means an amount necessary to achieve a selected result. Such an amount can be readily determined without undue experimentation by a person of ordinary skill in the art.

As used herein, the term "substantial" means being largely but not wholly that which is specified.

As used herein, the term "COX inhibitor" refers to a composition of compounds that is capable of inhibiting the activity or expression of COX-2 enzymes or is capable of inhibiting or reducing the severity, including pain and swelling, of a severe inflammatory response.

As used herein, the terms "derivatives" or a matter "derived" refer to a chemical substance related structurally to another substance and theoretically obtainable from it, that is, a substance that can be made from another substance. Derivatives can include compounds obtained via a chemical reaction. Methods of making derivatives of compounds are well known to those skilled in the art.

As used herein, the term "inflammatory cell" refers to those cellular members of the immune system, for example B and T lymphocytes, neutrophils or macrophages, involved in synthesis of prostaglandins in response to inflammatory signals such as interleukins, tumor necrosis factor, bradykinin, histamine or bacterial-derived components.

As used herein, the term "target cells" refers to that cell population in which the inhibition of PGE$_2$ or other prostaglandin synthesis is desired, such as inflammatory cells or tumor cells. Alternatively, "non-target cells" refers to that cell population in which the inhibition of PGE$_2$ or other prostaglandin synthesis is not desired, such as the gastric mucosal, neural or renal cells.

As used herein, the term "hop extract" refers to the solid material resulting from (1) exposing a hops plant product to a solvent, (2) separating the solvent from the hops plant products, and (3) eliminating the solvent.

As used herein, the term "solvent" refers to a liquid of aqueous or organic nature possessing the necessary characteristics to extract solid material from the hop plant product. Examples of solvents would include, but are not limited to, water, steam, superheated water, methanol, ethanol, hexane, chloroform, methylene chloride, liquid or supercritical CO$_2$, liquid N$_2$, or combinations of such materials.

As used herein, the term "CO$_2$ extract" refers to the solid material resulting from exposing a hops plant product to a liquid or supercritical CO$_2$ preparation followed by the removing of the CO$_2$.

As used herein, the term "spent hops" refers to the solid and hydrophilic residue from extract of hops.

As used herein, the term "alpha acid" refers to compounds collectively known as humulones and can be isolated from hops plant products including, among others, humulone, cohumulone, adhumulone, hulupone, and isoprehumulone.

As used herein, the term "isoalpha acid" refers to compounds isolated from hops plant products and which subsequently have been isomerized. The isomerization of alpha acids can occur thermally, such as boiling. Examples of isoalpha acids include, but are not limited to, isohumulone, isocohumulone, and isoadhumulone.

As used herein, the term "reduced isoalpha acid" refers to alpha acids isolated from hops plant product and which subsequently have been isomerized and reduced, including cis and trans forms. Examples of reduced isoalpha acids (RIAA) include, but are not limited to, dihydro-isohumulone, dihydro-isocohumulone, and dihydro-isoadhumulone.

As used herein, the term "tetra-hydroisoalpha acid" refers to a certain class of reduced isoalpha acid. Examples of tetra-hydroisoalpha acid (THIAA) include, but are not limited to, tetra-hydro-isohumulone, tetra-hydro-isocohumulone and tetra-hydro-isoadhumulone.

As used herein, the term "hexa-hydroisoalpha acid" refers to a certain class of reduced isoalpha acid. Examples of hexa-hydroisoalpha acids (HHIAA) include, but are not limited to, hexa-hydro-isohumulone, hexa-hydro-isocohumulone and hexa-hydro-isoadhumulone.

As used herein, the term "beta-acid fraction" refers to compounds collectively known as lupulones including, among others, lupulone, colupulone, adlupulone, tetrahydroisohumulone, and hexahydrocolupulone.

As used herein, the term "essential oil fraction" refers to a complex mixture of components including, among others, myrcene, humulene, beta-caryophyllene, undecane-2-on, and 2-methyl-but-3-en-ol.

As used herein, the term "methylxanthine" refers to a compound classified as a methylated xanthine derivative, including but not limited to caffeine; theobromine; theophylline; aminophylline; doxofylline; pentoxifylline; 8-oxopentoxifylline; 8-oxolisofylline; and lisofylline. Exemplary methylxanthines are illustrated in FIG. 5, including caffeine; theophylline; 1-proparagyl 3,7-dimethyl xanthine; 7-proparagyl 1,3-dimethyl xanthine; 3-proparagyl 1,7-dimethyl xanthine; 1,3,7-triproparagyl xanthine; 3-isobutyl-1-methylxanthine (IBMX); 1,3,7-tripropyl xanthine; 7-benzyl-IBMX; 1-propyl 3,7-dimethyl xanthine; 1,3-dipropyl 7-methyl xanthine; 1,3-dipropyl 7-proparagyl xanthine; 3,7-dimethyl 1-propyl xanthine; and 7-ally 1,3-dimethyl xanthine. Various methylxanthines are well known in the art (see, for example, Daly et al., *Pharmacol.* 42:309-321 (1991); Ukena et al., *Life Sci.* 39:743-750 (1986); Choi et al., *Life Sci.* 43:387-398 (1988); Daly et al., *J. Med. Chem.* 29:1305-1308 (1986); Daly et al., *Prog. Clin. Biol. Res.* 230:41-63 (1987), each of which is incorporated herein by reference).

As used herein, the term "curcuminoid" refers to a compound classified as a curcumin or derivative thereof, including but not limited to curcumin, demethoxycurcumin, bis-demethoxycurcumin, cis-trans-curcumin and cyclocurcumin. Exemplary curcuminoids are illustrated in FIG. 4.

As used herein, "conjugates" of compounds means compounds covalently bound or conjugated to a member selected from the group consisting of mono- or di-saccharides, amino acids, sulfates, succinate, acetate, and glutathione. The mono- or di-saccharide can be a member selected from the group consisting of glucose, mannose, ribose, galactose, rhamnose, arabinose, maltose, and fructose.

The invention relates to using hops extracts to reduce inflammation. Hop extraction in one form or another goes back over 150 years to the early nineteenth century when extraction in water and ethanol was first attempted. Even today, an ethanol extract is available in Europe, but by far the predominant extracts are organic solvent extracts (for example, hexane) and $CO_2$ extracts (supercritical and liquid). $CO_2$ (typically at 60 bars pressure and 50 to 10° C.) is in a liquid state and is a relatively mild, non-polar solvent highly specific for hop soft resins and oils. Beyond the critical point, typically at 300 bars pressure and 60° C., $CO_2$ has the properties of both a gas and a liquid and is a much stronger solvent. The composition of the various extracts is compared in Table 2.

At its simplest, hop extraction involves milling, pelleting and re-milling the hops to spread the lupulin, passing a solvent through a packed column to collect the resin components and finally, removal of the solvent to yield a whole or "pure" resin extract.

TABLE 2

| | Hop extracts (Percent w/w) | | | |
|---|---|---|---|---|
| Component | Hops | Organic Solvent | Super-Critical $CO_2$ | Liquid $CO_2$ |
| Total resins | 12-20 | 15-60 | 75-90 | 70-95 |
| Alpha-acids | 2-12 | 8-45 | 27-55 | 30-60 |
| Beta-acids | 2-10 | 8-20 | 23-33 | 15-45 |
| Essential oils | 0.5-1.5 | 0-5 | 1-5 | 2-10 |
| Hard resins | 2-4 | 2-10 | 5-11 | None |
| Tannins | 4-10 | 0.5-5 | 0.1-5 | None |
| Waxes | 1-5 | 1-20 | 4-13 | 0-10 |
| Water | 8-12 | 1-15 | 1-7 | 1-5 |

The main organic extractants are strong solvents and in addition to virtually all the lupulin components, they extract plant pigments, cuticular waxes, water and water-soluble materials.

Supercritical $CO_2$ is more selective than the organic solvents and extracts less of the tannins and waxes and less water and hence water-soluble components. It does extract some of the plant pigments like chlorophyll but rather less than the organic solvents do. Liquid $CO_2$ is the most selective solvent used commercially for hops and hence produces the most pure whole resin and oil extract. It extracts hardly the hard resins or tannins, much lower levels of plant waxes, no plant pigments and less water and water-soluble materials.

As a consequence of this selectivity and the milder solvent properties, the absolute yield of liquid $CO_2$ extract per unit weight of hops is less than when using the other mentioned solvents. Additionally, the yield of alpha acids with liquid $CO_2$ (89-93%) is lower than that of supercritical $CO_2$ (91-94%) or the organic solvents (93-96%). Following extraction, there is the process of solvent removal, which for organic solvents involves heating to cause volatilization. Despite this, trace amounts of solvent do remain in the extract. The removal of $CO_2$, however, simply involves a release of pressure to volatize the $CO_2$.

As shown in FIG. 3, hops $CO_2$ extracts can be fractionated into components, including hops oils, beta acids, and alpha acids. Hops oils include, but are not limited to, humulene, beta-caryophyllene, myrcene, farnescene, gamma-cadinene, alpha-selinene, and alpha-cadinene. Beta acids include, but are not limited to, lupulone, colupulone, adlupulone, tetrahydroisohumulone, and hexahydrocolupulone, collectively known as lupulones. Beta acids can be isomerized and reduced. Beta acids are reduced to give tetra-beta acids. Alpha acids include, but are not limited to, humulone, cohumulone, adhumulone, hulupone, and isoprehumulone. Alpha acids can be isomerized to give isoalpha acids. Iso-alpha acids can be reduced to give reduced-isoalpha acids, tetra-hydroisoalpha acids, and hexa-hydroisoalpha acids.

The identification of humulone from hops extract as an inhibitor of bone resorption is reported in Tobe et al. (*Biosci. Biotech. Biochem* 61(1):158-159 (1997)). Later studies by the same group characterized the mechanism of action of humulone as inhibition of COX-2 gene transcription following TNFalpha stimulation of MC3T3, E1 cells (Yamamoto, *FEBS Letters* 465:103-406 (2000)). It was concluded that the action of humulone (also humulon) was similar to that of glucocorticoids, but that humulone did not function through the glucocorticoid receptor. While these results establish that humulone inhibits $PGE_2$ synthesis in MC3T3 cells (osteoblasts) at the gene level, one skilled in the art would not assume that these results would necessarily occur in immune inflammatory cells or other cell lines. As disclosed herein, hops compounds and derivatives exhibit a high degree of tissue selectivity in target and non-target cell. Furthermore, the hops derivatives described in the present invention are structurally distinct from the alpha acid humulone.

The invention provides compositions containing at least one fraction isolated or derived from hops (*Humulus lupulus*). Examples of fractions isolated or derived from hops are alpha acids, isoalpha acids, reduced isoalpha acids, tetra-hydroisoalpha acids, hexa-hydroisoalpha acids, beta acids, and spent hops. Fractions isolated or derived from hops, include, but are not limited to, cohumulone, adhumulone, isohumulone, isocohumulone, isoadhumulone, dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone. Preferred compounds can also bear substituents, such as halogens, ethers, and esters.

Compounds of the fractions isolated or derived from hops can be represented by a supragenus below:

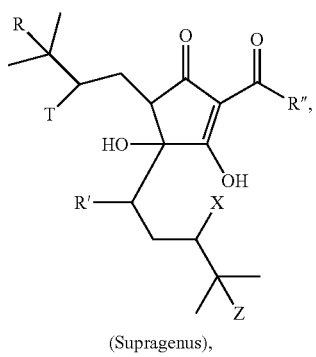

(Supragenus), wherein R' is selected from the group consisting of carbonyl, hydroxyl, OR, and OCOR, wherein R is alkyl; wherein R" is selected from the group consisting of $CH(CH_3)_2$, $CH_2CH(CH_3)_2$, and $CH(CH_3)CH_2CH_3$; and wherein R, T, X, and Z are independently selected from the group consisting of H, F, Cl, Br, I, and π orbital, with the proviso that if one of R, T, X, or Z is a π orbital, then the adjacent R, T, X, or Z is also a π orbital, thereby forming a double bond.

In another embodiment, compounds of the fractions isolated or derived from hops can be represented by a genus below:

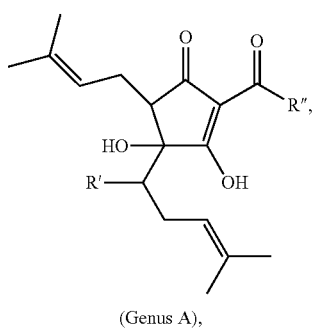

(Genus A), wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$. Exemplary Genus A structures include isoalpha acids such as isohumulone, isocohumulone, isoadhumulone, and the like, and reduced isoalpha acids such as dihydro-isohumulone, dihydro-isocohumulone, dihydro-isoadhumulone, and ether or ester conjugates or halogenated modifications of the double bond.

In yet another embodiment, compounds of the fractions isolated or derived from hops can be represented by a genus below:

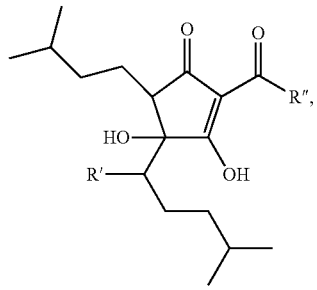

(Genus B), wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$. Exemplary Genus B structures include tetra-hydroisoalpha acids such as tetra-hydro-isohumulone, tetra-hydro-isocohymulone and tetra-hydro-adhumulone, and the like, and hexa-hydroisoalpha acids such as hexa-hydro-isohumulone, hexa-hydro-isocohumulone and hexa-hydro-isoadhumulone, and ether or ester conjugates.

As shown in FIG. 3, examples of compounds of an ingredient isolated or derived from hops, include, but are not limited to, humulone, cohumulone, adhumulone, isohumulone, isocohumulone, isoadhumulone, dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone. The compounds can bear substituents, as shown in the formula above.

Hops derivatives are known compounds occurring naturally in plants and found in food products and beverages. They may be prepared by any of the extraction and processing methods known in the art. Hops derivatives can be prepared directly from plant material in any known manner. The hops derivatives may be purified by methods known in the art, for example, by recrystallization from aqueous organic solvents such as aqueous alcohols. Synthetic modifications of hops derivatives may be prepared according to methods known in the pharmaceutical art of drug modification.

The invention also provides compositions containing a fraction or compounds isolated or derived from hops in combination with a curcuminoid methylxanthine. In one embodiment, the invention provides a composition containing a fraction or compounds isolated or derived from hops, as disclosed herein, and curcuminoid such as curcumin or a methylxanthine such as caffeine. Also in accordance with the present invention there are provided pharmaceutical compositions comprising an effective amount of a fraction isolated or derived from hops in combination with a curcuminoid or methylxanthine and optionally combination with a pharmaceutical diluent or adjuvant.

Dosage

Further in accordance with the present invention there are provided pharmaceutical formulations of oral dosage forms comprising an effective amount of hops derivatives for release of the active ingredient at a desired site in the gastrointestinal tract, for instance either in the stomach and/or duodenum according to known formulation techniques, for example, slow releasing tablets. Still further in accordance with the invention, there are provided pharmaceutical compositions comprising an effective tolerated amount of hops derivatives. Due to its low toxicity, high dosages of hops derivatives can be employed to produce useful results, depending upon the particular effect that is desired.

Hops derivatives are particularly suitable for oral administration. Therefore, hops derivatives can be formulated for oral use, namely: tablets, coated tablets, dragees, capsules, powders, granulates and soluble tablets, and liquid forms, for example, suspensions, dispersions or solutions, optionally together with an additional active ingredient, such as a curcuminoid or methylxanthine.

The invention extends to a method of preparing such pharmaceutical compositions as described herein and compositions when so prepared. The compositions may be manufactured by a method which comprises mixing hops derivatives with a pharmaceutically acceptable carrier or auxiliary, and optionally with an analgesic and/or anti-inflammatory substance and/or another compound(s). Methods for preparing a pharmaceutical composition are well known to those skilled in the art (see, for example, Genarro, ed., *Remington's Pharmaceutical Sciences*, 18th ed., Mack Publishing Co., Easton, Pa. (1990)).

The selected dosage level will depend upon the activity of the particular composition, the route of administration, the severity of the condition being treated or prevented, and the condition and prior medical history of the patient being treated. However, it is within the skill of the art to start doses of the composition at levels lower than required to achieve the desired therapeutic effect and to gradually increase the dosage until the desired effect is achieved. If desired, the effective daily dose may be divided into multiple doses for purposes of administration, for example, two to four separate doses per day. It will be understood, however, that the specific dose level for any particular patient will depend upon a variety of factors including body weight, general health, diet, time and route of administration, combination with other compositions and the severity of the particular condition being treated or prevented.

The invention provides methods that include delivering an effective amount of hops fractions, hops compounds, or hops derivatives. For example, a daily dose of compositions of the invention can be formulated to deliver about 0.5 to about 10,000 mg of a hops fraction, for example, alpha acid, isoalpha acid, reduced isoalpha acid, tetra-hydroisoalpha acid, hexa-hydroisoalpha acid, beta acid, spent hops, or other hops fractions, per day. In particular, an effective daily dose of compositions can be formulated to deliver about 50 to about 7500 mg of hops fraction, for example, alpha acids, isoalpha acid, reduced isoalpha acid, tetra-hydroisoalpha acid, hexa-hydroisoalpha acid, beta acid, spent hops, or other hops fractions, per day. For example, an effective daily dose of compositions can be formulated to deliver about 100 mg to about 5000 mg, about 200 mg to about 3000 mg, about 300 mg to about 2000 mg, about 500 to about 1000 mg of hops fraction per day. In one embodiment, the effective daily dose is administered once or twice a day. A certain embodiment provides a composition comprising about 0.5 to about 500 mg of isoalpha acid or reduced isoalpha acid, for example, about 50 to about 300 mg or about 100 to about 200 mg of isoalpha acid or reduced isoalpha acid per day. In another embodiment, the invention provides a composition comprising about 10 to about 3000 mg of reduced isoalpha acid, tetra-hydroisoalpha acid, or hexa-hydroisoalpha acid per day, for example, about 50 to about 2000 mg, about 100 to about 1000 mg, about 200 to about 750 mg, or about 250 to about 500 mg of reduced isoalpha acid, tetra-hydroisoalpha acid, or hexa-hydroisoalpha acid per day. Yet another certain embodiment provides a composition comprising about 50 to about 7500 mg of spent hops per day, for example, about 100 to about 6000 mg, about 200 to about 5000 mg, about 300 to about 3000 mg, about 500 to about 2000 mg, or about 1000 to about 1500 mg of spent hops per day.

A composition of embodiments for topical application can contain about 0.001 to about 10 weight percent, for example, about 0.01 to about 5 weight percent, or about 0.1 to about 1 weight percent, of a hops derivative. Such compositions can produce serum concentrations in the range of about 0.0001 to about 10 µM, for example, about 0.001 to about 5 µM, about 0.01 to 1 µM, or about 0.1 to about 0.5 µM of a fraction isolated or derived from hops or conjugate thereof.

In a composition of the invention in which one or more fraction isolated or derived from hops is combined with a curcuminoid, ratios of the fraction isolated or derived from hops to a curcuminoid can be varied to optimize a desired effect. For example, as disclosed herein, synergy of $PGE_2$ inhibition by a combination of RIAA and curcumin was observed in human aortic endothelial cells (HAEC (see Example 3). Synergy between RIAA and curcumin for inhibition of $PGE_2$ biosynthesis was observed at 100:1, 10:1 and 3:2 ratios of RIAA:curcumin. Particularly effective synergy was observed at a 3:2 ratio of RIAA:curcumin. The invention provides a composition containing a fraction isolated or derived from hops in combination with a curcuminoid such as curcumin. In one embodiment, the invention provides a combination of a fraction isolated or derived from hops, such as RIAA, and a curcuminoid such as curcumin in an amount and ratio effective to synergistically inhibit $PGE_2$. The fraction isolated or derived from hops, such as RIAA, and curcuminoid is combined in an effective ratio to synergistically inhibit $PGE_2$, for example, a fraction isolated or derived from hops, such as RIAA, to curcuminoid ratio of about 100:1 to about 1:10, for example, about 100:1, about 90:1, about 80:1, about 70:1, about 60:1, about 50:1, about 40:1, about 30:1, about 20:1, or about 10:1, about 5:1, about 4:1, about 3:1, about 2:1, about 3:2, about 1:1, about 1:2, about 1:3, about 1:4, about 1:5 or about 1:10. A particularly useful ratio of a fraction derived from hops to curcuminoid is about 3:2.

Similarly, a composition of the invention in which one or more fraction isolated or derived from hops is combined with a methylxanthine, ratios of the fraction isolated or derived from hops to a methylxanthine can be varied to optimize a desired effect. For example, as disclosed herein, synergy of $PGE_2$ inhibition by a combination of RIAA and caffeine was observed in RAW 264.7 macrophage cells (see Example 4). Synergy between RIAA and caffeine for inhibition of $PGE_2$ biosynthesis was observed at 100:1 to 1:100 ratios of RIAA: caffeine. The invention provides a composition containing a fraction isolated or derived from hops in combination with a methylxanthine. In one embodiment, the invention provides a combination of a fraction isolated or derived from hops, such as RIAA, and a methylxanthine, such as caffeine, in an amount and ratio effective to synergistically inhibit $PGE_2$. The fraction isolated or derived from hops, such as RIAA, and the methylxanthine are combined in an effective ratio to synergistically inhibit $PGE_2$, for example, a fraction isolated or derived from hops, such as RIAA, to a methylxanthine ratio of about 100:1 to about 1:100, for example, about 100:1, about 90:1, about 80:1, about 70:1, about 60:1, about 50:1, about 40:1, about 30:1, about 20:1, or about 10:1. Particularly useful ratios of a fraction isolated or derived from hops to methylxanthine include, for example, about 3:2, about 1:1, about 1:2, about 1:3, about 1:4, about 1:5, about 1:10, about 1:15, about 1:20, about 1:25, about 1:30, about 1:35, about 1:40, about 1:45, about 1:50, about 1:55, about 1:60, about 1:65, about 1:70, about 1:75, about 1:80, about 1:85, about 1:90, about 1:95, or about 1:100. A particularly useful methylxanthine is caffeine.

Formulations

Compositions of the invention can be administered in the form of a dietary supplement or therapeutic composition. The compositions may be administered orally, topically, transdermally, transmucosally, parenterally, and the like, in appropriate dosage units, as desired. Compositions for dietary application may include various additives such as other natural components of intermediary metabolism, vitamins and minerals, as well as inert ingredients such as talc and magnesium stearate that are standard excipients in the manufacture of tablets and capsules. For example, one embodiment comprises active ingredients of compositions of the invention in combination with glucosamine or chondrotin sulfate.

As used herein, "pharmaceutically acceptable carrier" includes solvents, dispersion media, coatings, isotonic and absorption delaying agents, sweeteners and the like, suitable for administration to an individual. These pharmaceutically acceptable carriers may be prepared from a wide range of materials including, but not limited to, diluents, binders and adhesives, lubricants, disintegrants, coloring agents, bulking agents, flavoring agents, sweetening agents and miscellaneous materials such as buffers and absorbents that may be needed in order to prepare a particular therapeutic composition. The use of such media and agents for pharmaceutically active substances is well known in the art. It is understood that formulations contain components that are compatible with the active ingredients. In one embodiment, talc, and magnesium stearate are included in the formulation. Other ingredients known to affect the manufacture of a composition of the invention as a dietary bar or functional food can include flavorings, sugars, amino-sugars, proteins and/or modified starches, as well as fats and oils.

Dietary supplements, lotions or therapeutic compositions of embodiments of the invention can be formulated in any manner known by one of skill in the art. In one embodiment, the composition is formulated into a capsule or tablet using techniques available to one of skill in the art. In capsule or tablet form, the recommended daily dose for an adult human or animal can be contained in one to six capsules or tablets. The compositions can also be formulated in other convenient forms, such as an injectable solution or suspension, a spray solution or suspension, a lotion, gum, lozenge, food or snack item. Food, snack, gum or lozenge items can include any ingestible ingredient, including sweeteners, flavorings, oils, starches, proteins, fruits or fruit extracts, vegetables or vegetable extracts, grains, animal fats or proteins. Thus, compositions of the invention can be formulated into cereals, snack items such as chips, bars, gumdrops, chewable candies or slowly dissolving lozenges. Compositions of the invention can be used for the treatment of inflammation-based diseases, both acute and chronic. Particularly useful formulations of compositions of the invention can reduce the inflammatory response and thereby promote healing of, or prevent further damage to, the affected tissue. A pharmaceutically acceptable carrier can also be used in the compositions and formulations of the invention.

Compositions of the invention can be used, for example, for the treatment of inflammation in a subject, and for treatment of other inflammation-associated disorders, such as an analgesic in the treatment of pain and headaches. The compositions of the invention can be used to treat a variety of conditions, including, for example, cancer, autoimmune diseases, inflammatory diseases, or neurological diseases. Compositions of the invention can also be used to treat conditions, such as HIV-1 infections, rhinovirus infections, and cardiovascular diseases. Compositions of the invention can be used to treat arthritis, including but not limited to rheumatoid arthritis, spondyloathopathies, gouty arthritis, osteoarthritis, systemic lupus erythematosis, and juvenile arthritis.

Compositions of the invention can additionally be used in the treatment of asthma, bronchitis, menstrual cramps, tendonitis, bursitis, and skin-related conditions such as psoriasis, eczema, burns and dermatitis. The compositions can also be used to treat gastrointestinal conditions such as inflammatory bowel disease, Crohn's disease, gastritis, irritable bowel syndrome and ulcerative colitis and for the prevention or treatment of cancer such as colorectal cancer.

Furthermore, compositions of the invention can be used in treating inflammation in such diseases as vascular diseases, migraine headaches, periarteritis nodosa, thyroiditis, aplastic anemia, Hodgkin's disease, sclerodma, rheumatic fever, type I diabetes, myasthenia gravis, multiple sclerosis, sacoidosis, nephrotic syndrome, Behchet's syndrome, polymyositis, gingivitis, hypersensitivity, swelling occurring after injury, myocardial ischemia, peridontal disease, fibromyalgia, atopic dermatitis, insulitis and the like. The compositions of the invention can also be used in the treatment of ophthalmic diseases, such as retinopathies, conjunctivitis, uveitis, ocular photophobia, and of acute injury to the eye tissue. Compositions of the invention can additionally be used in the treatment of pulmonary inflammation, such as that associated with viral infections and cystic fibrosis.

In addition, compositions of the invention can be used for the treatment of certain nervous system disorders such as cortical dementias including Alzheimer's disease. The compositions of the invention can also be used in the treatment of allergic rhinitis, respiratory distress syndrome, endotoxin shock syndrome, atherosclerosis, and central nervous system damage resulting from stroke, ischemia and trauma.

In one embodiment, the invention provides a composition comprising a fraction isolated or derived from hops and a methylxanthine. The fraction isolated or derived from hops can be selected from the group of alpha acids, isoalpha acids, reduced isoalpha acids, tetra-hydroisoalpha acids, hexa-hydroisoalpha acids, beta acids, and spent hops. The fraction isolated or derived from hops can also be a compound of a supragenus having the formula:

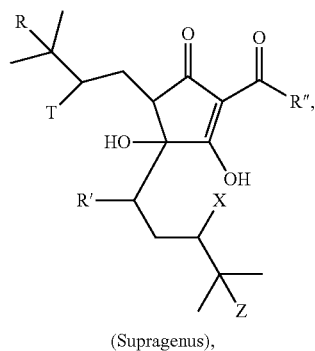

(Supragenus), wherein is selected from the group consisting of carbonyl, hydroxyl, OR, and OCOR, wherein R is alkyl; wherein R" is selected from the group consisting of $CH(CH_3)_2$, $CH_2CH(CH_3)_2$, and $CH(CH_3)CH_2CH_3$; and wherein R, T, X, and Z are independently selected from the group consisting of H, F, Cl, Br, I, and π orbital, with the proviso that if one of R, T, X, or Z is a π orbital, then the adjacent R, T, X, or Z is also a π orbital, thereby forming a double bond.

The fraction isolated or derived from hops can additionally comprise a compound of Genus A having the formula:

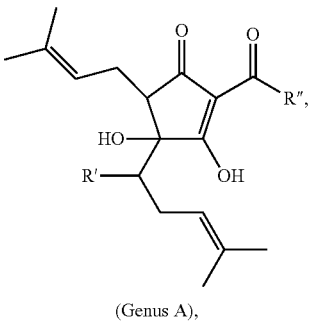

(Genus A), wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$.

In another embodiment, the fraction isolated or derived from hops can comprise a compound of Genus B having the formula:

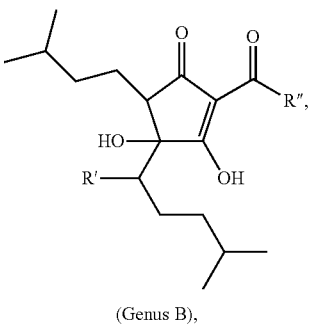

(Genus B), wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$.

In an embodiment, the fraction isolated or derived from hops can comprise a compound selected from the group consisting of humulone, cohumulone, adhumulone, isohumulone, isocohumulone, isoadhumulone, dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone.

In a composition of the invention, a methylxanthine can be selected from caffeine; theobromine; theophylline; aminophylline; doxofylline; pentoxifylline; 8-oxopentoxifylline; 8-oxolisofylline; lisofylline; 1-proparagyl 3,7-dimethyl xanthine; 7-proparagyl 1,3-dimethyl xanthine; 3-proparagyl 1,7-dimethyl xanthine; 1,3,7-triproparagyl xanthine; 3-isobutyl-1-methylxanthine (IBMX); 1,3,7-tripropyl xanthine; 7-benzyl-IBMX; 1-propyl 3,7-dimethyl xanthine; 1,3-dipropyl 7-methyl xanthine; 1,3-dipropyl 7-proparagyl xanthine; 3,7-dimethyl 1-propyl xanthine; and 7-allyl 1,3-dimethyl xanthine. In one embodiment, the fraction isolated or derived from hops and methylxanthine are in a ratio of about 100:1 to about 1:100. In another embodiment, the fraction isolated or derived from hops is reduced isoalpha acid and the methylxanthine is caffeine.

The composition can comprise about 0.5 to 10000 mg of the fraction isolated or derived from hops, or about 50 to 7500 mg of the fraction isolated or derived from hops. In addition, the composition can comprise about 0.001 to 10 weight percent of the fraction isolated or derived from hops. In another embodiment, the composition can comprise about 0.1 to 1 weight percent of the fraction isolated or derived from hops. The compositions of the invention can further comprise a pharmaceutically acceptable carrier and can be formulated for administration orally, topically, parenterally, or rectally.

In another embodiment, the invention provides a composition comprising a fraction derived from hops and a curcuminoid. In such a composition, the fraction derived from hops can be selected from isoalpha acids, reduced isoalpha acids, tetra-hydroisoalpha acids, hexa-hydroisoalpha acids, and beta acids.

In still another embodiment of such a composition, the fraction derived from hops can comprise a compound of a supragenus having the formula:

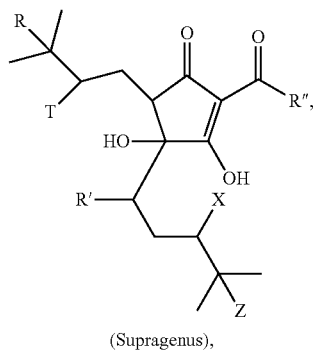

(Supragenus), wherein R' is selected from the group consisting of carbonyl, hydroxyl, OR, and OCOR, wherein R is alkyl; wherein R" is selected from the group consisting of $CH(CH_3)_2$, $CH_2CH(CH_3)_2$, and $CH(CH_3)CH_2CH_3$; and wherein R, T, X, and Z are independently selected from the group consisting of H, F, Cl, Br, I, and π orbital, with the proviso that if one of R, T, X, or Z is a π orbital, then the adjacent R, T, X, or Z is also a π orbital, thereby forming a double bond.

In yet another embodiment of such a composition, the fraction derived from hops comprises a compound of Genus A having the formula:

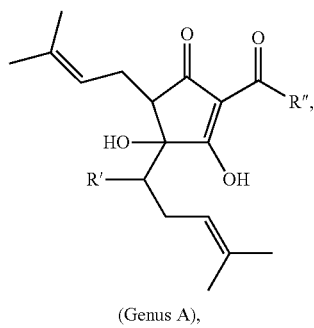

(Genus A), wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$.

In a further embodiment of such a composition, the fraction derived from hops can comprise a compound of Genus B having the formula:

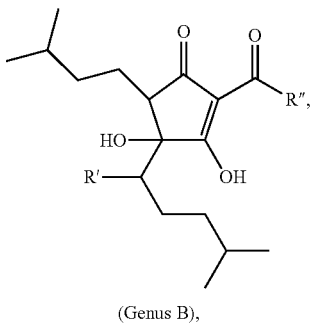

(Genus B), wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$.

In such a composition, the fraction derived from hops can comprise a compound selected from the group consisting of isohumulone, isocohumulone, isoadhumulone, dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone. In such a composition of the invention, the curcuminoid can be selected from curcumin, demethoxycurcumin, bisdemethoxycurcumin, cis-trans-curcumin and cyclocurcumin. In one embodiment, the fraction derived from hops and the curcuminoid are in a ratio of about 100:1 to about 1:10. In another embodiment, the ratio of the fraction derived from hops and the curcuminoid is about 3:2. In a particular embodiment, the fraction isolated from hops is reduced isoalpha acid and the curcuminoid is curcumin.

As discussed above, the composition can comprise about 0.5 to 10000 mg of the fraction isolated or derived from hops, or about 50 to 7500 mg of the fraction isolated or derived from hops. In addition, the composition can comprise about 0.001 to 10 weight percent of the fraction isolated or derived from hops. In another embodiment, the composition can comprise about 0.1 to 1 weight percent of the fraction isolated or derived from hops. The compositions of the invention can further comprise a pharmaceutically acceptable carrier and can be formulated for administration orally, topically, parenterally, or rectally.

The invention additionally provides a method of reducing inflammation by administering a composition of the invention. Such a method can be used to treat a variety of inflammatory conditions, as disclosed herein.

Besides being useful for human treatment, embodiments of the invention are also useful for treatment of other animals, including horses, dogs, cats, birds, sheep, pigs, and the like. Formulations for the treatment of inflammation can inhibit the induction and activity of COX-2 with little effect on the synthesis of $PGE_2$ in the gastric mucosa. Historically, the NSAIDs used for treatment of inflammation lacked the specificity of inhibiting COX-2 without affecting $PGE_2$ synthesis in gastric mucosal cells. Therefore, these drugs irritated and damaged the gastrointestinal system when used for extended periods. Such contraindications are not associated with the present invention and therefore, the formulations described my be used for extended periods with limited or no gastropathy. Administration can be by any method available to the skilled artisan, for example, by oral, topical, transdermal, transmucosal, or parenteral routes.

The invention additionally provides a method of reducing inflammation by administering an isoalpha acid or reduced isoalpha acid isolated from hops and a methylxanthine, such as caffeine (see Example 4). Other hops derivatives or a fraction isolated or derived from hops can also be administered with a methylxanthine such as caffeine to reduce inflammation. Methylxanthines such as caffeine and other methylated xanthine derivatives can be synthesized or isolated from natural sources such as coffee beans, tea leaves, guarana seeds, and the like. Guarana (*Paullinia cupana*) is a source of multiple methylxanthines, including caffeine and thoephylline.

As used herein, "reducing inflammation" refers to decreasing, ameliorating or inhibiting an inflammatory response. One skilled in the art can readily recognize a reduction in a sign or symptom associated with an inflammatory response. Reducing inflammation can refer to decreasing the severity of a sign or symptom associated with inflammation as well as inhibiting inflammation so that few or no symptoms associated with inflammation are presented.

The invention further provides a method of inhibiting inflammation by administering an isoalpha acid or reduced isoalpha acid isolated from hops and a curcuminoid such as curcumin (see Example 3). Other hops derivatives or a fraction isolated or derived from hops can also be administered with a curcuminoid such as curcumin to reduce inflammation.

As used herein, the terms "curcuminoid" and "active curcuminoid" refer to species within the curcuminoid genera that is capable of inhibiting the inducibility and/or activity of COX-2 while having or no effect on COX-1 or is capable of inhibiting or reducing the severity of an inflammatory response. The curcuminoid can be extracted from natural products or chemically synthesized.

A yellow pigmented fraction isolated from the rhizomes of *Curcuma longa* contains curcuminoids belonging to the dicinnamoyl methane group. Curcuminoids are present to the extent of 3 to 5 percent. They are considered the most important active ingredients and are believed to be responsible for the biological activity of *Curcuma longa*. Though their major activity is anti-inflammatory, curcuminoids have been reported to possess antioxidant, anti-allergic, wound healing, antispasmodic, antibacterial, antifungal and antitumor activity as well. Curcumin (FIG. 4B) was isolated in 1815 and structurally defined in 1910. Other curcuminoids isolated from *Curcum longa* include demethoxycurcumin (FIG. 4C), bisdemethoxycurcumin (FIG. 4D), a cis-trans geometrical isomer of curcumin (FIG. 4E), and cyclocurcumin (FIG. 4F). Curcuminoids may be found in other botanicals in addition to *Curcuma longa*, such as *Curcuma xanthorrhiza* and *Curcuma zedoaria*.

Curcuminoids are well known for their anti-inflammatory activity. Tumeric is one of the oldest anti-inflammatory drugs used in Ayurvedic medicine. The anti-inflammatory activity of curcuminoids has been evaluated in inflammatory reaction models such as chemical or physical irritants like carrageenin, cotton pellets, formaldehyde and the granuloma pouch. Human, double-blinded, clinical trials have demonstrated efficacy in rheumatoid arthritis at a dose of 1200 mg curcuminoids/day for five to six weeks. At these doses, however, signs of gastrointestinal (GI) discomfort and stomach irritation are frequently reported. The GI upset and stomach irritation caused by high doses of curcuminoids may be due to the fact that curcuminoids act on prostaglandin production in a manner similar to that of aspirin and aspirin-like anti-inflammatory agents.

Preferably, the curcuminoid genus, as represented in FIG. 4A, and specifically exemplified by curcumin FIG. 4B is a pharmaceutical grade botanical extract such as can be obtained commercially, for example, from Sabinsa (121 Ethel Road West, Piscataway, N.J.). Other curcuminoids that may be employed include demethoxycurcumin (FIG. 4C), bis-demethoxycurcumin (FIG. 4D), a cis-trans curcumin (FIG. 4E), and cyclocurcumin (FIG. 4F). The curcuminoid used can be readily obtained from *Curcuma longa* L. Pharmaceutical grade curcuminoid extract is standardized to have a curcuminoid content of greater than about 70 percent. The pharmaceutical, botanical grade extract can be assayed for safety and efficacy. As employed in the embodiments of the invention, the extract has a curcuminoid content of about 1 to 99 percent by weight. The minimum curcuminoid content is generally about 70 percent by weight, and can be, for example, at least about 75%, at least about 80%, at least about 85%, at least about 90%, at least about 95%, or greater. Alternatively, the curcuminoid may be synthesized using standard techniques known in chemical synthesis.

In a composition containing a fraction isolated or derived from hops, for example, RIAA, IAA, THIAA or HHIAA, and a curcuminoid, the composition can be formulated to deliver about 0.5 to about 5000 mg of curcuminoid per day. In particular, an effective daily dose can be formulated to deliver about 5 to about 2000 mg of curcuminoid per day, for example, about 10 to about 1500 mg, about 20 to about 1000 mg, about 50 to about 500 mg, or about 100 to about 200 mg. In an embodiment of the invention, the composition can be formulated to provide an effective daily dose to be administered once or twice a day. In one embodiment, a composition can contain about 200 mg of a curcuminoid, and about 300 mg of a fraction isolated or derived from hops to be administered once or twice a day. In a particular embodiment, a composition can contain about 200 mg of a curcuminoid and about 300 mg of RIAA. In addition, a composition of the invention can contain, in a particular embodiment, about 200 mg of a curcuminoid and about 300 mg of IAA. Also, a composition of the invention can contain about 200 mg of a curcuminoid and about 300 mg of THIAA or HHIAA.

In a composition containing a fraction isolated or derived from hops and a methylxanthine such as caffeine or theophylline, the composition of the invention can be formulated to deliver about 0.5 to about 5000 mg of a methylxanthine per day. In particular, an effective daily dose can be formulated to deliver about 5 to about 2000 mg of a methylxanthine per day, for example, about 10 to about 1500 mg, about 20 to about 1000 mg, about 50 to about 500 mg, or about 100 to about 200 mg. For example, the composition can be formulated to provide an effective daily dose to be administered once or twice a day. In a particular embodiment, a composition can contain about 100 mg of methylxanthine, for example, caffeine or a derivative of caffeine such as theophylline, and 300 mg of RIAA to be administered once or twice a day.

Assay Using AGS Cell Line

The discovery of COX-2 has made possible the design of drugs that reduce inflammation without removing the protective prostaglandins (PGs) in the stomach and kidney made by COX-1. As disclosed herein, compositions of the invention can be assessed using in vitro animal cells to assess COX-2 and COX-1 inhibitory activity employing $PGE_2$, which has cytoprotective actions and plays a role in maintaining the integrity of the gastrointestinal mucosa, as an endpoint. Secondarily, different cell types are used to confirm results. The screening process can be used to indicate compositions that have specific COX-2 activity and limited COX-1 inhibition. Compositions of embodiments of the invention can be tested in two cell types: 1) human pulmonary cells or other cell line to determine and identify optimal amounts and ratios for compositions comprising more than one component; and 2) human gastric epithelial cells (AGS cell line), a gastrointestinal tract cell line and a model system for assessing toxicity that is typically related to inhibition of COX-1, which is required for wound healing (such as ulcers). Hence, compositions of embodiments of the invention that can inhibit COX-2 or COX-2 induction can be screened by selecting compositions that have low or no activity in AGS cells and good activity in human pulmonary cells or other cell lines.

As disclosed herein, a variety of assays are available to show the effectiveness of one or more fractions isolated or derived from hops (see examples). It is understood by those skilled in the art that a fraction isolated or derived from hops, as disclosed herein, can be assayed for activity in reducing inflammation using a variety of assays well known to those skilled in the art, including those exemplified herein.

The following examples are intended to illustrate but are not intended to limit the scope of the invention.

Example 1

AGS Gastric Mucosal Cells Constitutively Express Both Cyclooxygenase-1 and Cyclooxygenase-2

Summary—This example demonstrates that the AGS human gastric mucosal cell line, possessing constitutive expression of COX-1 and COX-2, is a model for assessing the gastrointestinal toxicity of cyclooxygenase-inhibiting compounds.

Equipment used in this example included: an OHAS Model #E01140 analytical balance, a Forma Model #F1214 biosafety cabinet (Marietta, Ohio), various pipettes to deliver 0.1 to 100 µL (VWR, Rochester, N.Y.), a cell hand tally counter (VWR Catalog #23609-102, Rochester, N.Y.), a Forma Model #F3210 $CO_2$ incubator (Marietta, Ohio), a hemacytometer (Hausser Model #1492, Horsham, Pa.), a Leica Model #DM IL inverted microscope (Wetzlar, Germany), a PURELAB Plus Water Polishing System (U.S. Filter, Lowell, Mass.), a 4° C. refrigerator (Forma Model #F3775, Marietta, Ohio), a vortex mixer (VWR Catalog #33994-306. Rochester, N.Y.), and a 37° C. water bath (Shel Lab Model #1203, Cornelius, Oreg.).

Chemicals and reagents—Prostaglandin $E_2$ EIA kit Monoclonal was purchased from Cayman Chemical (Ann Arbor, Mich.). Anti-COX-1 and anti-COX-2 rabbit polyclonal antisera were obtained from Upstate Biotechnology (Lake Placid, N.Y.); donkey anti-goat IgG-HRP was procured from Santa Cruz Biotechnology (Santa Cruz, Calif.). Heat inactivated Fetal Bovine Serum (FBS-HI Cat. #35-011CV), and Dulbecco's Modification of Eagle's Medium (DMEM Cat #10-013CV) was purchased from Mediatech (Herndon, Va.). All standard reagents were obtained from Sigma (St. Louis, Mo.) and were the purest commercially available.

Cell Culture—The human gastric mucosal cell line AGS was obtained from the American Type Culture Collection (ATCC number CRL-1739; Manassas, Va.) and sub-cultured according to the instructions of the supplier. The cells were routinely cultured at 37° C. with 5% $CO_2$ in RPMI 1640 containing 10% FBS, with 50 units penicillin/mL, 50 µg streptomycin/mL, 5% sodium pyruvate, and 5% L-glutamine. Exponentially growing cells were seeded into 6-well plates and grown to confluence. A 20 µL aliquot of the supernatant media was sampled for determination of $PGE_2$ content. Cells were then washed in PBS, scraped and lysed for immunoblotting.

Protein assay—Protein concentrations of cell lysates were determined using the NanoOrange Protein Quantitation Kit with bovine serum albumin as the standard (Molecular Probes, Eugene, Oreg.) according to the procedure supplied by the manufacturer. Fluorescence was determined using a Packard FluoroCount, Model BF 10000 fluorometer with the excitation filter set at 485 nm and emission filter set at 570 nm using Packard PlateReader version 3.0 software. The I-Smart program provided with the Packard PlateReader was used to calculate the protein concentration.

Immunoblotting—Western blotting of COX-1 and COX-2 was performed using PAGErTM Gold Precast Gels (Bio Whittaker Molecular Applications (Rockland, Me.). AGS cell lysates containing approximately 60 µg protein were loaded with Laemmli Sample Buffer into the wells of the gel in a total volume of 30 µL. The vertical minigel electrophoresis chambers were made by Savant Instruments Inc. (Holbrook, N.Y.), model MV 120. Gels were run at 40 mA/plate (constant current) at room temperature until the bromophenol blue stain reached the bottom of the gel, about one hour. Gels were then blotted on the polyvinyl fluoride transfer membranes (Pall Corporation, Ann Arbor, Mich.), overnight, at 500 mA and 4° C. Precision Protein Standard molecular weight markers, unstained, broad range (BioRad, Hercules, Calif.) were used. The BioWest™ Extended duration chemiluminescent substrate, a non-isotopic, horseradish peroxidase substrate kit for Western blot detection (BioImaging Systems, Upland, Calif.) was used for protein visualization. Images of western blots were acquired using a UVP Epi Chemi II Darkroom (BioImaging Systems), analyzed and enhanced by LabWorks™ Image Acquisition and Analysis Software (BioImaging Systems).

$PGE_2$ assay—A commercial, non-radioactive procedure for quantification of $PGE_2$ was employed (Caymen Chemical, Ann Arbor, Mich.) and the recommended procedure of the manufacturer was used without modification. Briefly, 25 µL of the medium, along with a serial dilution of $PGE_2$ standard samples, were mixed with appropriate amounts of acetylcholinesterase-labeled tracer and $PGE_2$ antiserum, and incubated at room temperature for 18 h. After the wells were emptied and rinsed with wash buffer, 200 µL of Ellman's reagent containing substrate for acetylcholinesterase were added. The reaction was carried out on a slow shaker at room temperature for 1 h and the absorbance at 415 nm was determined. The $PGE_2$ concentration was represented as picograms per $10^5$ cells.

Results—The AGS cell line constitutively expresses both COX-1 and COX-2, with COX-1 expression approximately 4-times greater than COX-2 expression. $PGE_2$ synthesis in AGS cells over 18 h was 660 pg/$10^5$ cells. Thus, this example demonstrates that the AGS human gastric mucosal cell line, possessing constitutive expression of COX-1 and COX-2, can serve as a model for assessing the gastrointestinal toxicity of cyclooxygenase-inhibiting compounds.

In the past, the classical COX-2 hypothesis has downplayed the role of COX-2 expression in the gastrointestinal mucosa. White in normal gastric mucosa COX-1 is the predominant COX isozyme, as demonstrated in this example and in the literature, there is increasing evidence that detectable amount of COX-2 mRNA and protein are both constitutively expressed and inducible in specific locations of the gastric mucosa in both animals and humans (Halter et al. Gut 49:443-453 (2001)). Recent studies in rats have shown that whereas selective inhibition of COX-1 or COX-2 is not ulcerogenic, combined inhibition of both COX-1 and COX-2 induces severe lesions in the stomach and small intestine comparable with the effects of NSAID such as indomethacin. This observation suggests an important contribution of COX-2 to the maintenance of gastrointestinal mucosal integrity.

Example 2

Inhibition of $PGE_2$ Synthesis in Stimulated and Nonstimulated Murine Macrophages by Hops (Humulus lupulus) Compounds and Derivatives Summary—This example illustrates that hops fractions and derivatives inhibit COX-2 synthesis of $PGE_2$ preferentially over COX-1 synthesis of $PGE_2$ in the RAW 264.7 murine macrophage model.

Chemicals and reagents—Bacterial lipopolysaccharide (LPS; B E. coli 055:B5) was from Sigma (St. Louis, Mo.). Hops fractions (1) alpha hop (1% alpha acids; AA), (2) aromahop OE (10% beta acids and 2% isomerized alpha acids, (3) isohop (isomerized alpha acids; IAA), (4) beta acid solution (beta acids BA), (5) hexahop gold (hexahydro isomerized alpha acids; HHIAA), (6) redihop (reduced isomerized-alpha acids; RIAA), (7) tetrahop (tetrahydro-iso-alpha acids; THIAA) and (8) spent hops were obtained from Betatech Hops Products (Washington, D.C., U.S.A.). The spent hops were extracted two times with equal volumes of absolute ethanol. The ethanol was removed by heating at 40° C. until a only thick brown residue remained. This residue was dissolved in DMSO for testing in RAW 264.7 cells. Unless otherwise noted, all standard reagents were obtained from Sigma (St. Louis, Mo.) and were the purest commercially available. All other chemicals and equipment were as described in EXAMPLE 1.

Cell culture—RAW 264.7 cells, obtained from American Type Culture Collection (Catalog #TIB-71, Manassas, Va.), were grown in Dulbecco's Modification of Eagle's Medium (DMEM, Mediatech, Herndon, Va.) and maintained in log phase. The DMEM growth medium was made by adding 50 mL of heat inactivated FBS and 5 mL of penicillin/streptomycin to a 500 mL bottle of DMEM and storing at 4° C. The growth medium was warmed to 37° C. in water bath before use.

On day one of the experiment, the log phase RAW 264.7 cells were plated at $8 \times 10^4$ cells per well in 0.2 mL growth medium per well in a 96-well tissue culture plate in the morning. At the end of the day one (6 to 8 h post plating), 100 µL of growth medium from each well were removed and replaced with 100 µL fresh medium.

A 1.0 mg/mL stock solution of LPS, used to induce the expression of COX-2 in the RAW 264.7 cells, was prepared by dissolving 1.0 mg of LPS in 1 mL DMSO. It was vortexed until dissolved and stored at 4° C. Before use, it was melted at room temperature or in a 37° C. water bath.

On day two of the experiment, test materials were prepared as 1000X stock in DMSO. In 1.7 mL microfuge tubes, 1 mL DMEM without FBS was added for test concentrations of 0.05, 0.10, 0.5, and 1.0 µg/mL. Two µL of the 1000X DMSO stock of the test material was added to the 1 mL of medium without FBS. The tube contained the final concentration of the test material concentrated 2-fold and was placed in an incubator for 10 minutes to equilibrate to 37° C.

For COX-2 associated $PGE_2$ synthesis, 100 µL of medium were removed from each well of the cell plates prepared on day one and replaced with 100 µL of equilibrated 2X final concentration of the test compounds. Cells were then incubated for 90 minutes. Twenty µL of LPS were added to each well of cells to be stimulated to achieve a final concentration of 10 ng LPS/mL and the cells were incubated for 4 h. Following the LPS stimulation, the appearance of the cells was observed, and cell viability was assessed by a 3-(4,5-dimethylthiazol-2-yl)-2,5-diphenyltetrazolium bromide (MTT)-based colorimetric assay (Sigma, St. Louis, Mo.). The MTT solution was added directly to the wells after sampling for $PGE_2$ determination. The absorbance of each well was read at 580 nm using an ELISA plate reader. No toxicity was observed at the highest concentrations tested for any of the compounds. Twenty-five μL of supernatant medium from each well was transferred to a clean microfuge tube for the determination of $PGE_2$ released into the medium. $PGE_2$ was assayed and reported as previously described in EXAMPLE 1.

For COX-1 associated $PGE_2$ synthesis, 100 μL of medium were removed from each well of the cell plates prepared on day one and replaced with 100 μL of equilibrated 2X final concentration of the test compounds. Cells were then incubated for 90 minutes. Next, instead of LPS stimulation, the cells were incubated with 100 μM arachidonic acid for 15 minutes. Twenty-five μL of supernatant medium from each well was transferred to a clean microfuge tube for the determination of $PGE_2$ into the medium. The appearance of the cells was observed and viability was determined as described above. No toxicity was observed at the highest concentrations tested for any of the compounds. Twenty-five μL of supernatant medium from each well was transferred to a clean microfuge tube for the determination of $PGE_2$ released into the medium. $PGE_2$ was determined and reported as previously described in EXAMPLE 1. The median inhibitory concentrations ($IC_{50}$) for $PGE_2$ synthesis from both COX-2 and COX-1 were calculated as described below.

The median inhibitory concentration ($IC_{50}$) for $PGE_2$ synthesis was calculated using CalcuSyn (BIOSOFT, Ferguson, Mo.). This statistical package performs multiple drug dose-effect calculations using the median effect methods described by Chou and Talaly, *Adv. Enzyme Regul.* 22:27-55, (1984), hereby incorporated by reference.

Briefly, the analysis correlates the "Dose" and the "Effect" in the simplest possible form: fa/fu=(C/Cm)m, where C is the concentration or dose of the compound and Cm is the median-effective dose signifying the potency. Cm is determined from the x-intercept of the median-effect plot. The fraction affected by the concentration of the test material is fa and the fraction unaffected by the concentration is fu (fu=1−fa). The exponent m is the parameter signifying the sigmoidicity or shape of the dose-effect curve. It is estimated by the slope of the median-effect plot.

The median-effect plot is a graph of x=log(C) vs y=log(fa/fu) and is based on the logarithmic form of Chou's median-effect equation. The goodness of fit for the data to the median-effect equation is represented by the linear correlation coefficient r of the median-effect plot. Usually, the experimental data from enzyme or receptor systems have an r>0.96, from tissue culture an r>0.90 and from animal systems an r>0.85. In the cell-based studies reported here, all linear correlation coefficients were greater than 0.90. Experiments were repeated three times on three different dates. The percent inhibition at each dose was averaged over the three independent experiments and used to calculate the median inhibitory concentrations reported.

TABLE 3

COX-2 and COX-1 inhibition in RAW 264.7 cells by hop fractions and derviatives

| Test Material | COX-2 $IC_{50}$ [μg/ml] | COX-1 $IC_{50}$ [μg/ml] | COX-1 $IC_{50}$/ COX-2 $IC_{50}$ |
|---|---|---|---|
| Genus A structures | | | |
| Isohop (IAA) | 0.13 | 18 | 144 |
| Redihop (RIAA) | 0.34 | 29 | 87 |
| Genus B structures | | | |
| Tetrahop (THIAA) | 0.20 | 4.0 | 21 |
| Hexahop (HHIAA) | 0.29 | 3.0 | 11 |
| Alpha acids | | | |
| Alpha hop (AA) | 0.21 | 6.2 | 30 |
| Others | | | |
| Aromahop OE | 1.6 | 4.1 | 2.6 |
| Beta acids (BA) | 0.54 | 29 | 54 |
| Spent hops (EtOH) | 0.88 | 21 | 24 |

As seen in Table 3, all hops fractions and derivatives selectively inhibited COX-2 over COX-1 in this target macrophage model. This was a novel and unexpected finding. The extent of COX-2 selectivity for the hops derivatives IAA and RIAA, respectively, 144- and 87-fold, was unanticipated. In this RAW 264.7 cell model, Genus A compounds exhibited a greater COX-2 selectivity than Genus B compounds, averaging 116-fold vs 16-fold, respectively, greater COX-2 inhibition. Alpha acid, beta acids and spent hops were also highly selective COX-2 inhibitors with COX-1/COX-2 ratios, respectively, 30, 54 and 24. Such high COX-2 selectivity combined with low median inhibitory concentrations, has not been previously reported for natural products from other sources. Aromahop was least COX-2 selective with a COX-1/COX-2 ratio of 2.6.

Example 3

Synergy of $PGE_2$ Inhibition Produced by Combinations of Reduced Isomerized Alpha Acids and Curcumin Extract in Human Aortic Endothelial Cells Summary—This example describes the effect of combinations of reduced isomerized alpha acids (RIAA) and curcumin on the inhibition of prostaglandin $E_2$ ($PGE_2$) production in the tumor necrosis factor-α, (TNFα)-stimulated human aortic endothelial model of inflammation.

The standard equipment used in these experiments is described in Example 1. Chemicals and reagents were obtained as follows. TNFα was from Sigma (St. Louis, Mo.). Prostaglandin E2 monoclonal antibody kit was purchased from Cayman Chemical (Ann Arbor, Mich.). Heat inactivated Fetal Bovine Serum (FBS-HI Cat, #35-011CV) and Dulbecco's Modification of Eagle's Medium (DMEM Cat #10-1013CV) was purchased from Mediatech (Herndon, Va.). Unless otherwise noted, all standard reagents were obtained from Sigma (St. Louis, Mo.) and were the purest commercially available. Test substances included RIAA obtained from Betatech Hops Products (Redihop (rho-iso-alpha acids (RIAA), 29.5-30.5%, <0.2% iso-alpha acids))(Washington, D.C.) and curcumin extract (06656) (Metagenics, Gig Harbor, Wash.). Other commercial sources of curcumin include Nutriscience Innovations (Fairfield Conn.).

Cell culture and treatment with test material—Human aortic endothelial cells (HAEC) were obtained from Cambrex (Catalog #CC-2525, Walkersville, Md.) and subcultured according to supplier instructions. For experiments, HAEC are grown in a T75 flask containing EGM-2 growth media (Cambrex #cc-4176; containing fetal bovine serum (FBS), hydrocortisone, hFGF-B, VEGF, R3-IGF-1, ascorbic acid, hEGF, GA-1000 (gentamicin/amphotericin B) and heparin) at 37° C. in a humidified 95% air/5% $CO_2$ atmosphere. Prior to cells becoming confluent, they were prepared for testing in microtiter plates by treating with a fresh trypsin solution and counted. Approximately $10^5$ cells/well were aliquoted into 96-well plates in 200 µL EGM-2 growth medium per well. Cells were allowed to reach 80% confluence before treatment with test material and TNF-α.

On the day of the experiment, the EGM-2 growth medium was aspirated and replaced with 200 µL EGM-2 containing the test material. The EGM-2 growth medium containing test material was formulated by adding 4 µL of 250X stock test material in dimethylsulfoxide (DMSO) to 1 mL of EGM-2. Thus, each well contained the same amount of DMSO. Control wells received DMSO in growth media only. The final concentrations of test material were 5, 1, 0.1 and 0.01 µg/mL. The test material was added before stimulation with 100 ng/ml TNFα.

Table 4 shows a dosing matrix for HAEC treated with test material followed by TNFα stimulation.

taining substrate for acetylcholinesterase were then added. The reaction was maintained on a slow shaker at room temperature for 1 h and the absorbance at 415 nm was determined in a Bio-tek Instruments (Model #Elx800, Winooski, Vt.) enzyme-linked immunosorbent assay (ELISA) plate reader. The manufacturer's specifications for this assay include intra-assay coefficient of variation of <10%, cross reactivity with $PGD_2$ and $PGF_{2\alpha}$ of less than 1% and linearity over the range of 10-1000 pg mL-1. The $PGE_2$ concentration was computed as pg $PGE_2$ per $10^5$ cells, as described below.

For calculations related to $PGE_2$ assays, the median inhibitory concentration ($IC_{50}$) for PGE2 synthesis was calculated using CalcuSyn (BIOSOFT, Ferguson, Mo.). This statistical package performs multiple drug dose-effect calculations using the median effect methods described by Chou and Talaly (*Adv. Enzyme Regul.* 22, 27-55 (1984)).

Briefly, the analysis correlates the "Dose" and the "Effect" in the simplest possible form: $fa/fu=(C/Cm)^m$, where C is the concentration or dose of the compound and Cm is the median-effective dose signifying the potency. Cm is determined from the x-intercept of the median-effect plot. The fraction affected by the concentration of the test material is fa and the fraction unaffected by the concentration is fu (fu=1−fa). The exponent m is the parameter signifying the sigmoidicity or shape of the dose-effect curve. It is estimated by the slope of the median-effect plot.

TABLE 4

Dosing matrix for HAEC treated with test material followed by TNFα stimulation.

| Compound | Fraction RIAA | | d1 [µg/mL] | d2 [µg/mL] | d3 [µg/mL] | d4 [µg/mL] | No. Wells |
|---|---|---|---|---|---|---|---|
| 1. BetaTech RIAA | 1.00 | | 5.000 | 1.000 | 0.100 | 0.010 | 8 |
| 2. Curcumin (06656) | 0.00 | | 5.000 | 1.000 | 0.100 | 0.010 | 8 |
| 3. RIAA:Curcumin [100:1] | 0.99 | | 5.000 | 1.000 | 0.100 | 0.010 | 8 |
| | | RIAA = | 4.950 | 0.990 | 0.099 | 0.0099 | |
| | | Curcumin = | 0.050 | 0.010 | 0.001 | 0.0001 | |
| 4. RIAA:Curcumin [10:1] | 0.91 | | 5.000 | 1.000 | 0.100 | 0.010 | 8 |
| | | RIAA = | 4.545 | 0.909 | 0.091 | 0.009 | |
| | | Curcumin = | 0.455 | 0.091 | 0.009 | 0.001 | |
| 5. RIAA:Curcumin [3:1] | 0.75 | | 5.000 | 1.000 | 0.100 | 0.010 | 8 |
| | | RIAA = | 3.750 | 0.750 | 0.075 | 0.0075 | |
| | | Curcumin = | 1.250 | 0.250 | 0.025 | 0.0025 | |
| 6. RIAA:Curcumin [3:2] | 0.60 | | 5.000 | 1.000 | 0.100 | 0.010 | 8 |
| | | RIAA = | 3.00 | 0.60 | 0.06 | 0.006 | |
| | | Curcumin = | 2.00 | 0.40 | 0.04 | 0.004 | |
| 7. RIAA:Curcumin [1:1] | 0.50 | | 5.000 | 1.000 | 0.100 | 0.010 | 8 |
| | | RIAA = | 2.50 | 0.50 | 0.05 | 0.005 | |
| | | Curcumin = | 2.50 | 0.50 | 0.05 | 0.005 | |
| 8. RIAA:Curcumin [2:3] | 0.40 | | 5.000 | 1.000 | 0.100 | 0.010 | 8 |
| | | RIAA = | 2.00 | 0.40 | 0.04 | 0.00 | |
| | | Curcumin = | 3.00 | 0.60 | 0.06 | 0.01 | |
| 9. RIAA:Curcumin [1:10] | 0.09 | | 5.000 | 1.000 | 0.100 | 0.010 | 8 |
| | | RIAA = | 0.455 | 0.091 | 0.009 | 0.001 | |
| | | Curcumin = | 4.545 | 0.909 | 0.091 | 0.009 | |
| 10. RIAA:Curcumin [1:100] | 0.010 | | 5.000 | 1.000 | 0.100 | 0.010 | 8 |
| | | RIAA = | 0.05 | 0.01 | 0.001 | 0.0001 | |
| | | Curcumin = | 4.95 | 0.99 | 0.099 | 0.0099 | |

Experiments in which the positive control for TNFα treatment of HAEC did not stimulate the cells were excluded.

Determination of $PGE_2$—A commercial, non-radioactive procedure for quantification of $PGE_2$ was employed (Caymen Chemical, Ann Arbor, Mich.) for the determination of $PGE_2$, and the recommended procedure of the manufacturer was used without modification. Briefly, 50 µL of the supernatant culture medium were diluted with appropriate amounts of acetylcholinesterase-labeled tracer and $PGE_2$ antiserum and incubated at room temperature for 18 h. Afterwards, the wells in the $PGE_2$-assay microtiter plate were emptied and rinsed with wash buffer; two-hundred µL of Ellman's reagent con- The median-effect plot is a graph of x=log(C) vs y=log(fa/fu) and is based on the logarithmic form of Chou's median-effect equation. The goodness of fit for the data to the median-effect equation is represented by the linear correlation coefficient r of the median-effect plot. Usually, the experimental data from enzyme or receptor systems have an r>0.96, from tissue culture an r>0.90 and from animal systems an r>0.85. In the cell-based studies reported here, all linear correlation coefficients were greater than 0.90. For most robust results, experiments are repeated a minimum of three times on three different dates. The percent inhibition at each dose is averaged over the three independent experiments and used to calculate the median inhibitory concentrations reported.

Synergy of test components was quantified using the combination index (CI) parameter. The CI of Chou-Talaly is based on the multiple drug-effect and is derived from enzyme kinetic models (Chou and Talalay, *J. Biol. Chem.* 252:6438-6442 (1977)). The equation determines only the additive effect rather than synergism or antagonism. Synergism is defined herein as a more than expected additive effect, and antagonism as a less than expected additive effect as proposed by Cho and Talalay, supra, 1977. Using the designation of CI=1 as the additive effect, for mutually exclusive compounds that have the same mode of action or for mutually non-exclusive drugs that have totally independent modes of action, the following relationships are obtained: CI<1, =1, and >1 indicating synergism, additivity and antagonism, respectively.

Cell viability—Cell viability was assessed by visual inspection of cells prior to or immediately following sampling of the medium for $PGE_2$ assay. Cell mortality was noted when observed.

For statistical methods, a minimum of four concentrations (Table 4) was used to compute dose-response curves and medium inhibitory concentrations ($IC_{50}$s) with 95% confidence intervals using CalcuSyn (BIOSOFT, Ferguson, Mo.). This statistical package performs multiple drug dose-effect calculations using the Median Effect methods described by Chou and Talaly (supra, 1984). All dose-response data captured the median inhibitory concentration. Two data transformations were applied where warranted. The first transformation consisted of computing the percent inhibition from the highest $PGE_2$ production produced from the lowest test concentration when the $PGE_2$ production of these low doses exceeded the $PGE_2$ production of the TNFα-stimulated control. This process controls for response variability and gradients throughout the plate. The second data transformation adjusted for variance in response at the graded doses. Monte Carlo simulations using the historical variance between wells predicted that dose-response curves appear graded only 40% of the time when duplicate wells per concentration are used in a four-point dose-response curve. Thus, sorting the response by concentration before calculating the $IC_{50}$ was done in those situations in which the response did not appear graded.

Results—The $IC_{50}$ of 0.81 μg/mL (95% confidence limit (CL) 0.19-3.4 μg/mL) obtained for RIAA in this study was consistent with previous results for RIAA using other models of inflammation such as the LPS-RAW 264.7 model. Curcumin exhibited a median inhibitory concentration of 1.4 μg/mL (95% CL 0.75-2.7), consistent with values reported in the literature for a variety of inflammation models. Examples of reported median inhibitory concentrations for curcumin include 1.8 to 3.6 μg/mL (5 to 10 μM) for inhibition of 12-O-tetradecanoylphorbol-13-acetate (TPA)-induced cyclooxygenase activity in mouse epidermis (Huang et al., *Cancer Res.* 51:813-819 (1991)); 63% inhibition at 5 μM curcumin of phorbol 12-myristate 13-acetate (PMA)-induced cyclooxygenase-2 (COX-2) mediated PGE2 biosynthesis in human gastrointestinal epithelial cells (Zhang et al., F., *Carcinogenesis* 20:445-451 (1999); and approximately 80% inhibition of COX-2 protein expression at 3.6 μg/mL in untreated HT-29 human colon cancer cells (Goel et al., *Cancer Letters* 172:111-118 (2001)). Studies of direct inhibition of COX-1 and COX-2 isozymes indicates rather high $IC_{50}$ values for PGE2 inhibition and low COX-2 selectivity, respectively, approximately 70 μg/mL and 2.1-fold (Ramsewak et al., *Phytomedicine* 7:303-308 (2000).

Median inhibitory concentrations for RIAA, curcumin and RIAA:curcumin combinations for TNFα-stimulated HAEC are presented in Table 5, with the regions of synergy computed for each combination. Synergy was noted for all RIAA:curcumin combinations, albeit at different segments of the dose-response curves. Regions of synergy were seen at both the low and high ends of the dose response curve and with combinations in which RIAA>curcumin also when RIAA<curcumin (for example, RIAA:curcumin 100:1 to 1:100). Thus, it is reasonable to expect synergy to occur in viva over a wide range of doses of both RIAA and curcumin regardless of the ratio of the components in the formulation dosed.

TABLE 5

Median inhibitory concentrations and regions of synergy for RIAA, curcumin and RIAA:eurcumin combinations in TNFα-stimulated HAEC.

| Test Material | RIAA [%] | $IC_{50}$ [μg/mL] | Region of Synergy RAA [μg/mL] |
|---|---|---|---|
| RIAA | 100 | 0.81 | |
| Curcumin | 0 | 1.4 | |
| RIAA:Curcumin [100:1] | 99 | 1.6 | 4.6-495 |
| RIAA:Curcumin [10:1] | 91 | 2.4 | 30-2266 |
| RIAA:Curcumin [3:1] | 75 | 1.3 | 0.000001-0.17 |
| RIAA:Curcumin [3:2] | 60 | 1.1 | 0.000004-0.36 |
| RIAA:Curcumin [1:1] | 50 | 1.7 | 0.00004-0.052 |
| RIAA:Curcumin [2:3] | 40 | 4.6 | 0.000026-0.013 |
| RIAA:Curcumin [1:10] | 9.1 | 2.9 | 0.000037-0.0018 |
| RIAA:Curcumin [1:100] | 1.0 | 2.0 | 0.0000082-0.000055 |

Region of synergy defined by CI < 1.0

HAEC were treated with test material 60 minutes prior to TNFα stimulation and incubated overnight. Eighteen hours post TNFα-stimulation, supernatant media was sampled for $PGE_2$ determination. Median inhibitory concentrations were computed from a minimum of four concentrations over three independent experiments. The CIs were computed as described above.

Figure 6A:
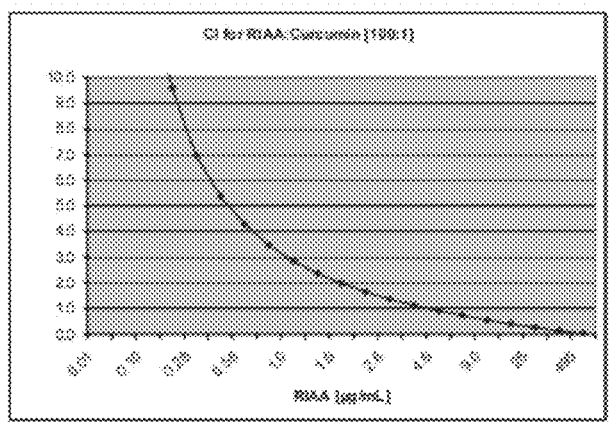
FIG. 6 shows a graphic representation of the computed Combination Index parameter versus the concentration of reduced isomerized alpha-acids (RIAA) for RIAA:curcumin ratios of 100:1 (FIG. 6A), 10:1 (FIG. 6B), 3:1 (FIG. 6C), 3:2, (FIG. 6D), 1:1 (FIG. 6E), 2:3 (FIG. 6F), 1:10 (FIG. 6G), 1:100 (FIG. 6H).
Figure 6B:
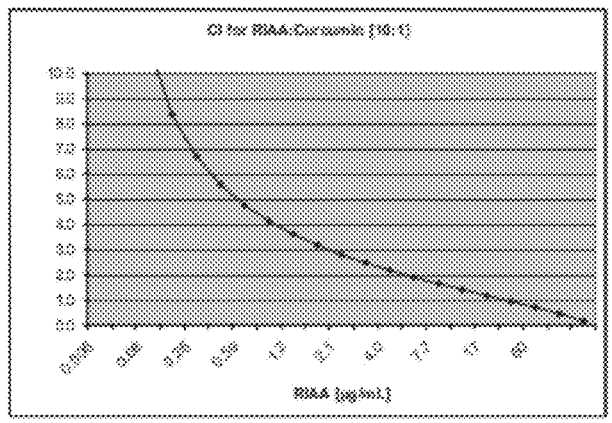
Figure 6C:
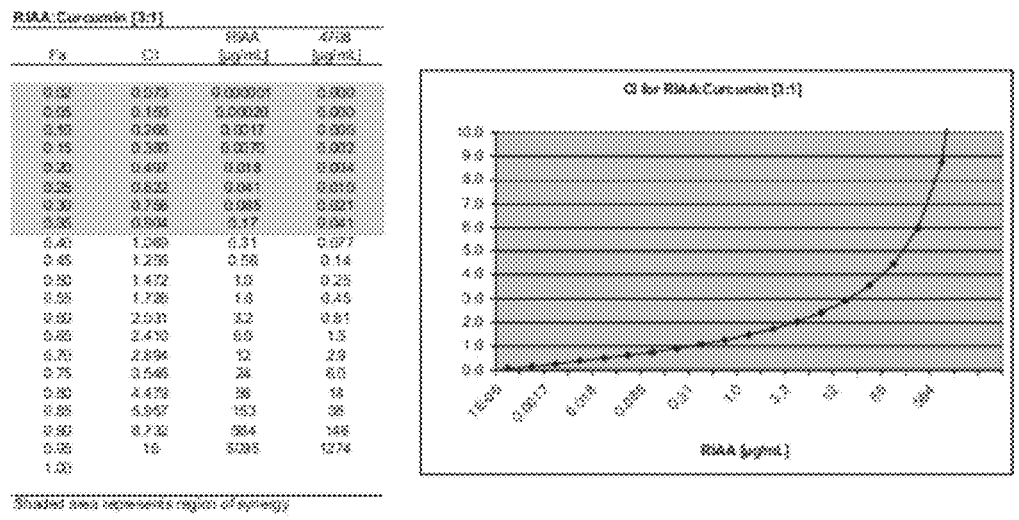
Figure 6D:
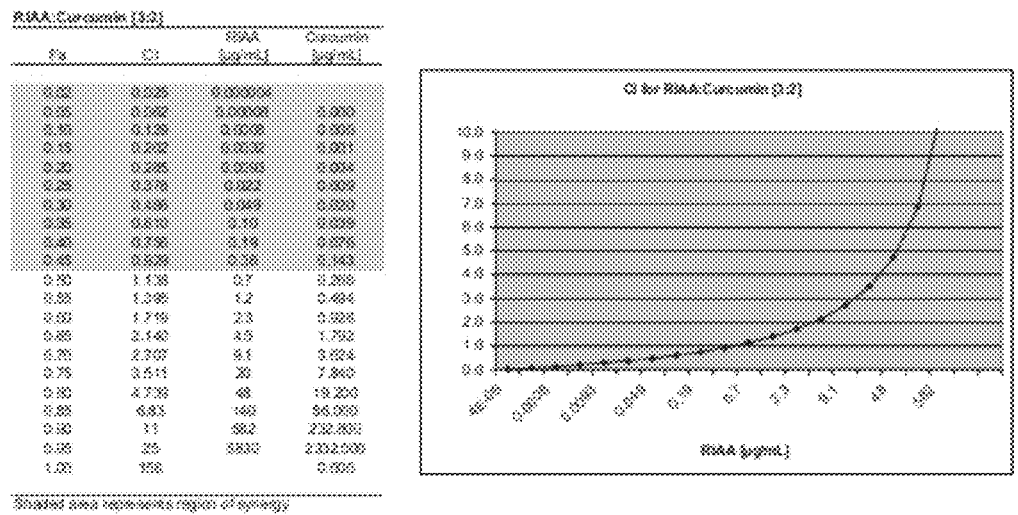
Figure 6E:
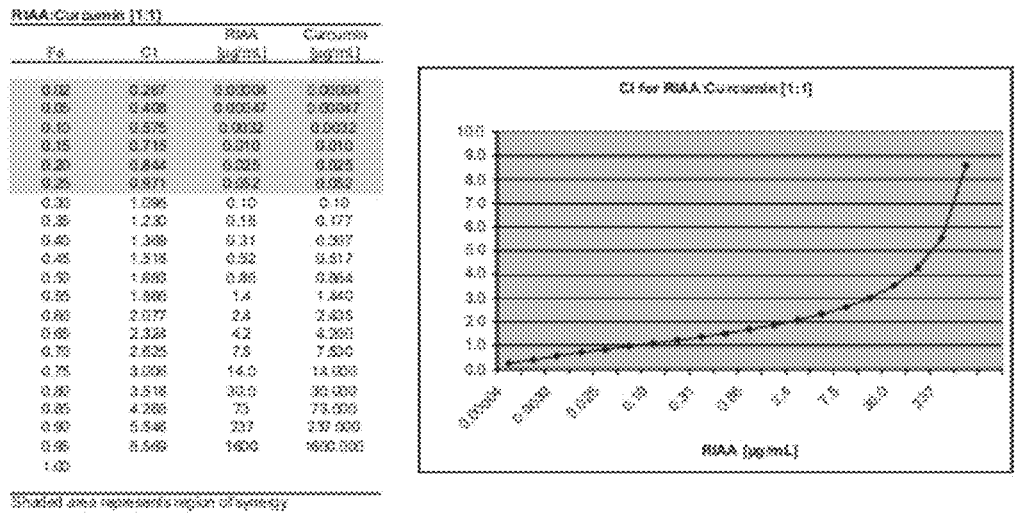
Figure 6F:
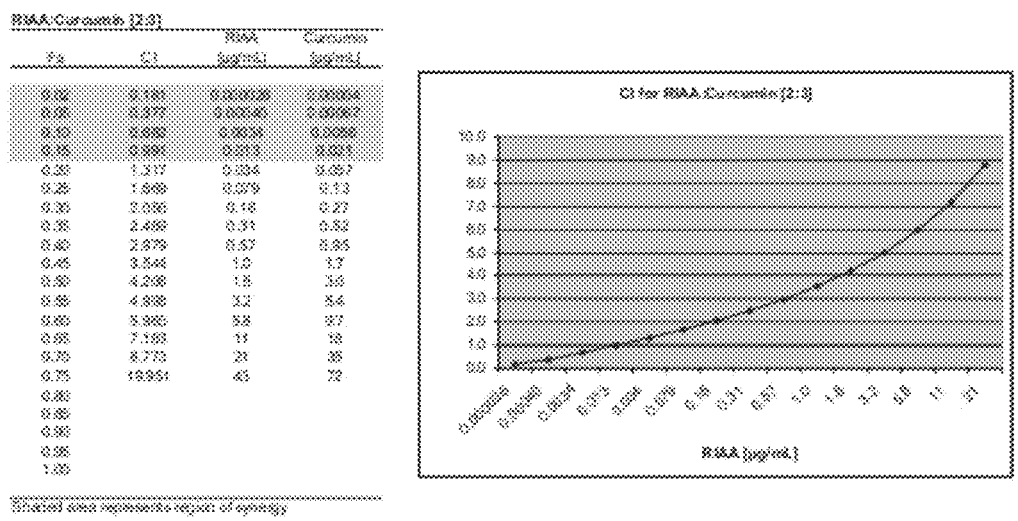
Figure 6G:
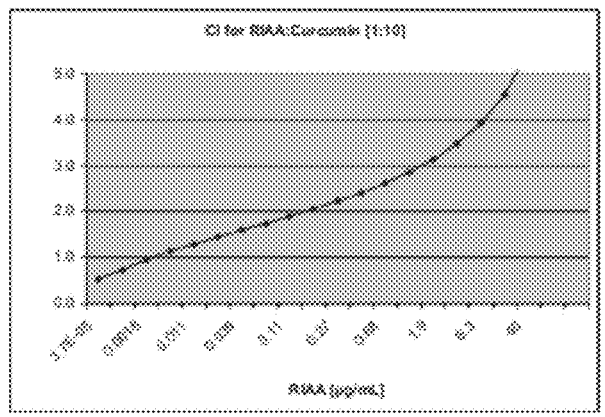
Figure 6H:
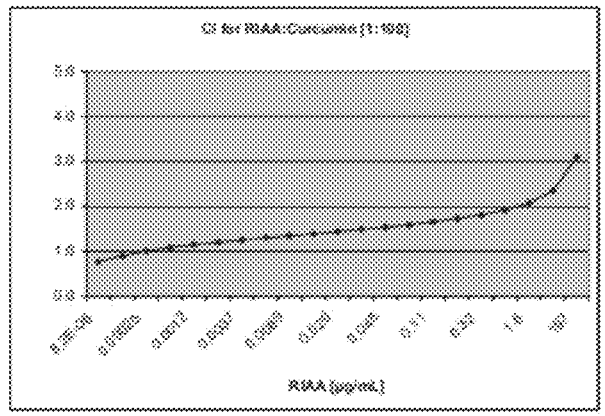

FIG. 6 shows a graphic representation of the computed Combination Index parameter versus the concentration of reduced isomerized alpha-acids (RIAA) for RIAA:curcumin ratios of 100:1 (FIG. 6A), 10:1 (FIG. 6B), 3:1 (FIG. 6C), 3:2 (FIG. 6D), 1:1 (FIG. 6E), 2:3 (FIG. 6F), 1:10 (FIG. 6G) 1:100 (FIG. 6H).

These results show that RIAA and curcumin extract are potent inhibitors of $PGE_2$ biosynthesis TNFα-stimulated HAEC. Synergy between RIAA and curcumin for inhibition of $PGE_2$ biosynthesis was observed at 100:1, 10:1 and 3:2 ratios of RIAA:curcumin. For the 100:1 and 10:1 combinations, this synergy occurred at the upper end of the dose-response curve and represented concentrations of RIAA greater than 3.4 and 30 μg/mL, respectively. Particularly effective synergy was observed at the 3:2 ratio of RIAA:curcumin, where the CI was less than 1 for concentrations of RIAA less than 0.36 μg/mL. Antagonism was more frequently observed than synergy for the RIAA:curcumin combinations tested. The most pronounced antagonism was noted at 40% RIAA with a significant increase in $IC_{50}$ to 4.6 μg/mL and a mean CI for the $IC_{50}$, $IC_{75}$ and $IC_{90}$ of 15.

Example 4

Synergy of $PGE_2$ Inhibition Produced by Combinations of Reduced Isomerized Alpha Acids and Caffeine in Raw 264.7 Cells This example describes the effect of combinations of RIAA and caffeine on the inhibition of $PGE_2$ production in the lipopolysaccharide (LPS)-stimulated RAW 264.7 model of inflammation.

The standard equipment used in these experiments is described in Example 1. Chemicals and reagents were obtained as follows. Bacterial lipopolysaccharide (LPS; B *E. coli* 055:B5) was from Sigma (St. Louis, Mo.). Prostaglandin $E_2$ monoclonal antibody kit was purchased from Cayman Chemical (Ann Arbor, Mich.). Heat inactivated Fetal Bovine Serum (FBS-HI Cat, #35-011CV) and Dulbecco's Modification of Eagle's Medium (DMEM Cat #10-1013CV) was purchased from Mediatech (Herndon, Va.). Unless otherwise noted, all standard reagents were obtained from Sigma (St. Louis, Mo.) and were the purest commercially available. Test substances included RIAA obtained from Betatech Hops Products (Redihop (rho-iso-alpha acids (RIAA), 29.5-30.5%, <0.2% iso-alpha acids) (Washington, D.C.), and caffeine (Sigma, St. Louis, Mo.).

Cell culture and treatment with test material—RAW 264.7 cells (ATTC number TIB-71) were obtained from the American Type Culture Collection (Manassas, Va.) and sub-cultured according to the instructions of the supplier. In preparation for testing, cells were grown in growth DMEM medium with 10% FBS-HI with penicillin/streptomycin and maintained in log phase prior to experimental setup. On day two of the experiment, cells were plated at $8 \times 10^4$ cells per well in a 96-well tissue culture plate with 200 μL growth medium per well.

Following overnight incubation at 37° C. with 5% $CO_2$, the growth medium was aspirated and replaced with 200 μL DMEM with no FBS or penicillin/streptomycin. Test materials were dissolved in DMSO as a 250-fold stock solution. Four μL of this 250-fold stock test material preparation was added to 1 mL of DMEM and 200 μL of this solution was added to wells in duplicate for each dose of test material. Final concentrations of test material were 10, 1, 0.1 and 0.01 μg/mL. LPS was added to stimulate COX-2 expression at a concentration of 1.0 μg/mL 60 minutes following the addition of the test materials. Table 6 shows the dosing matrix for RAW 264.7 cells treated with test material and LPS stimulation. Data from experiments in which LPS stimulation was ineffective or in which RIAA results were significantly different from historical values were excluded from the determination of the median inhibitory concentrations and RIAA:caffeine synergy.

TABLE 6

Dosing matrix for RAW 264.7 cells treated with test material and LPS stimulation.

| Compound | Fraction RIAA | | d1 [μg/mL] | d2 [μg/mL] | d3 [μg/mL] | d4 [μg/mL] | No. Wells |
|---|---|---|---|---|---|---|---|
| 1. BetaTech RIAA | 1.00 | | 10.000 | 1.000 | 0.100 | 0.010 | 8 |
| 2. Caffeine | 0.00 | | 50.000 | 5.000 | 1.000 | 0.100 | 8 |
| 3. RIAA:Caffeine [100:1] | 0.99 | | 10.000 | 1.000 | 0.100 | 0.010 | 8 |
| | | RIAA = | 9.901 | 0.990 | 0.099 | 0.0099 | |
| | | Caffeine = | 0.099 | 0.010 | 0.001 | 0.0001 | |
| 4. RIAA:Caffeine [10:1] | 0.91 | | 10.000 | 1.000 | 0.100 | 0.010 | 8 |
| | | RIAA = | 9.091 | 0.909 | 0.091 | 0.009 | |
| | | Caffeine = | 0.909 | 0.091 | 0.009 | 0.001 | |
| 5. RIAA:Caffeine [3:1] | 0.75 | | 10.000 | 1.000 | 0.100 | 0.010 | 8 |
| | | RIAA = | 7.500 | 0.750 | 0.075 | 0.0075 | |
| | | Caffeine = | 2.500 | 0.250 | 0.025 | 0.0025 | |
| 6. RIAA:Caffeine [3:2] | 0.60 | | 10.000 | 1.000 | 0.100 | 0.010 | 8 |
| | | RIAA = | 6.00 | 0.60 | 0.06 | 0.006 | |
| | | Caffeine = | 4.00 | 0.40 | 0.04 | 0.004 | |
| 7. RIAA:Caffeine [1:1] | 0.50 | | 10.000 | 1.000 | 0.100 | 0.010 | 8 |
| | | RIAA = | 5.00 | 0.50 | 0.05 | 0.005 | |
| | | Caffeine = | 5.00 | 0.50 | 0.05 | 0.005 | |
| 8. RIAA:Caffeine [2:3] | 0.40 | | 10.000 | 1.000 | 0.100 | 0.010 | 8 |
| | | RIAA = | 4.00 | 0.40 | 0.04 | 0.00 | |
| | | Caffeine = | 6.00 | 0.60 | 0.06 | 0.01 | |
| 9. RIAA:Caffeine [1:10] | 0.09 | | 10.000 | 1.000 | 0.100 | 0.010 | 8 |
| | | RIAA = | 0.909 | 0.091 | 0.009 | 0.001 | |
| | | Caffeine = | 9.091 | 0.909 | 0.091 | 0.009 | |
| 10. RIAA:Caffeine [1:100] | 0.010 | | 10.000 | 1.000 | 0.100 | 0.010 | 8 |
| | | RIAA = | 0.10 | 0.01 | 0.001 | 0.0001 | |
| | | Caffeine = | 9.90 | 0.99 | 0.099 | 0.0099 | |

Assays for $PGE_2$ were performed essentially as described in Example 3.

Cell viability—Cell viability was assessed by visual inspection of cells prior to or immediately following sampling of the medium for $PGE_2$ assay. Cell mortality was noted when observed.

Statistical methods were performed essentially as described in Example 3 except that the first transformation consisted of computing the percent inhibition from the highest $PGE_2$ production produced from the lowest test concentration when the $PGE_2$ production of these low doses exceeded the $PGE_2$ production of the LPS-stimulated control.

Results—The $IC_{50}$ of 1.3 μg/mL (95% confidence limit (CL) 0.41-3.9 μg/mL) obtained for RIAA in this study was consistent with previous results for RIAA in this laboratory using the LPS-RAW 264.7 overnight protocol. The median $PGE_2$ inhibitory concentration for caffeine of 25 μg/mL (95% CL 4.6-138) in this study was consistent with the value of 8.2 μg/mL recently reported in the literature (Fiebich et al., *Neuropharmacology* 39:2205-2213 (2000)). $IC_{50}$ and CI values for RIAA, caffeine and RIAA:caffeine combinations are presented in Table 7.

Median inhibitory concentrations for RIAA, caffeine and RIAA:caffeine combinations for LPS-stimulated RAW 264.7 cells are presented in Table 7, with the regions of synergy computed for each combination. Synergy was noted for all RIAA:caffeine combinations, albeit at different segments of the dose-response curves. Regions of synergy were seen at the upper portion of the dose-response curves for RIAA:caffeine combinations from 100:1 to 3:2 and throughout the entire dose-response curve for combinations of 1:1 and greater.

Thus, it is reasonable to expect synergy to occur in vivo over a wide range of doses of both RIAA and caffeine regardless of the ratio of the components in the formulation dosed.

TABLE 7

Median inhibitory concentrations and regions of synergy for RIAA, caffeine and RIAA:caffeine combinations in LPS-stimnlated RAW264.7 cells.

| Test | RIAA [%] | IC50 [µg/mL] | Region of Synergy RIAA [µg/mL] |
|---|---|---|---|
| RIAA | 10 | 1. | |
| Caffeine | 0 | 2 | |
| RIAA:Caffeine [100:1] | 9 | 2. | 3.1-1360 |
| RIAA:Caffeine [10:1] | 9 | 3. | 697-2.4 × 10⁸ |
| RIAA:Caffeine [3:1] | 7 | 1. | 2.7-1.6 × 10⁷ |
| RIAA:Caffeine [3:2] | 6 | 1. | 1.1-251 |
| RIAA:Caffeine [1:1] | 5 | 0.9 | 3.8 × 10⁻-5.8 × 10⁵ |
| RIAA:Caffeine [2:3] | 4 | 1 | 1.5 × 10⁻-18 |
| RIAA:Caffeine [1:10] | 9. | 1. | 2.1 × 10⁻-9.4 × 10⁷ |
| RIAA:Caffeine [1:100] | 1. | 1. | 5.7 × 10⁻-47705 |

Region of synergy defined by CI < 1.0

RAW 264.7 cells were treated with test material 60 minutes prior to LPS stimulation and incubated overnight. Eighteen hours post LPS-stimulation, supernatant media was sampled for $PGE_2$ determination. Median inhibitory concentrations were computed from a minimum of four concentrations over two independent experiments. The CIs were computed as described.

Figure 7A:
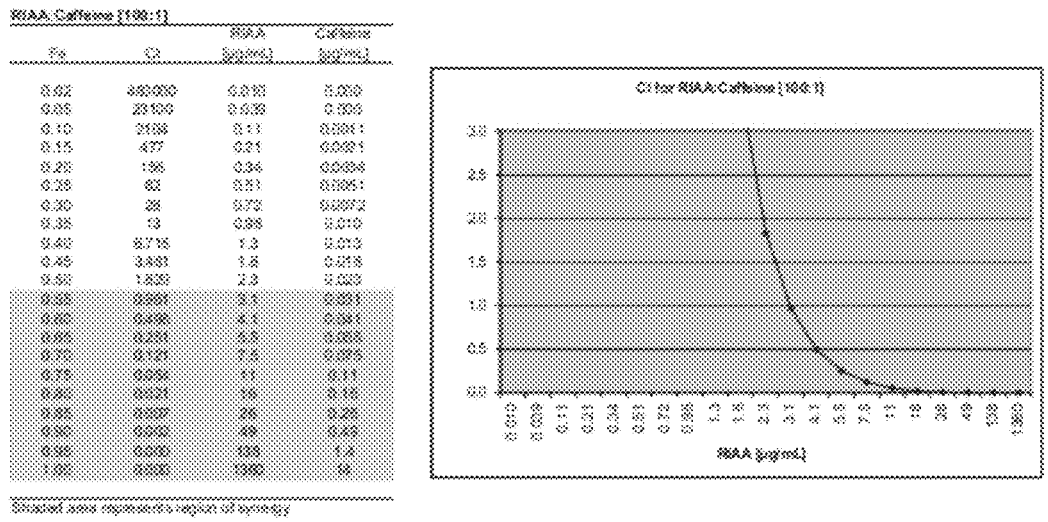
FIG. 7 shows a graphic representation of the computed Combination Index parameter versus the concentration of reduced isomerized alpha-acids (RIAA) for RIAA:caffeine ratios of 100:1 (FIG. 7A), 10:1 (FIG. 7B), 3:1 (FIG. 7C), 3:2, (FIG. 7D), 1:1 (FIG. 7E), 2:3 (FIG. 7F); 1:10 (FIG. 7G), 1:100 (FIG. 7H).
Figure 7B:
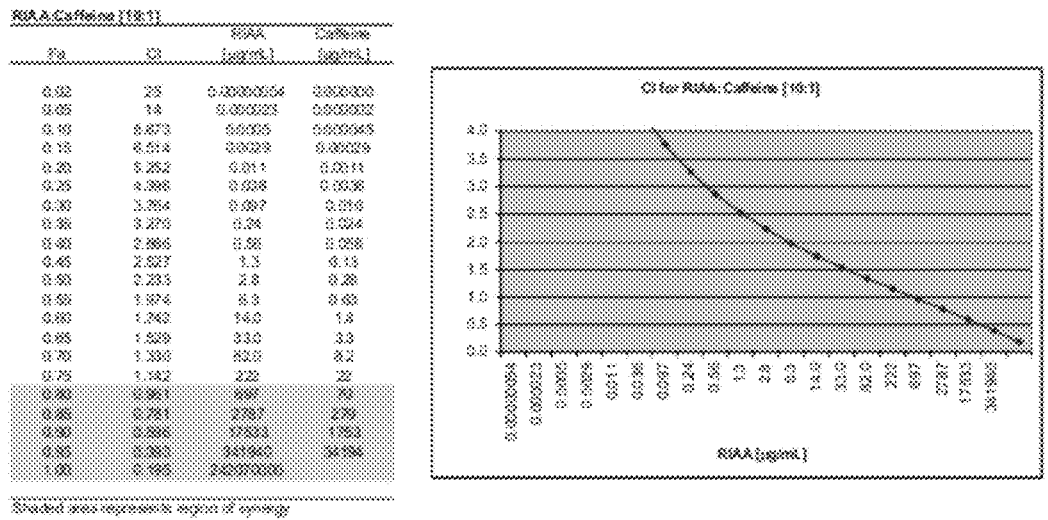
Figure 7C:
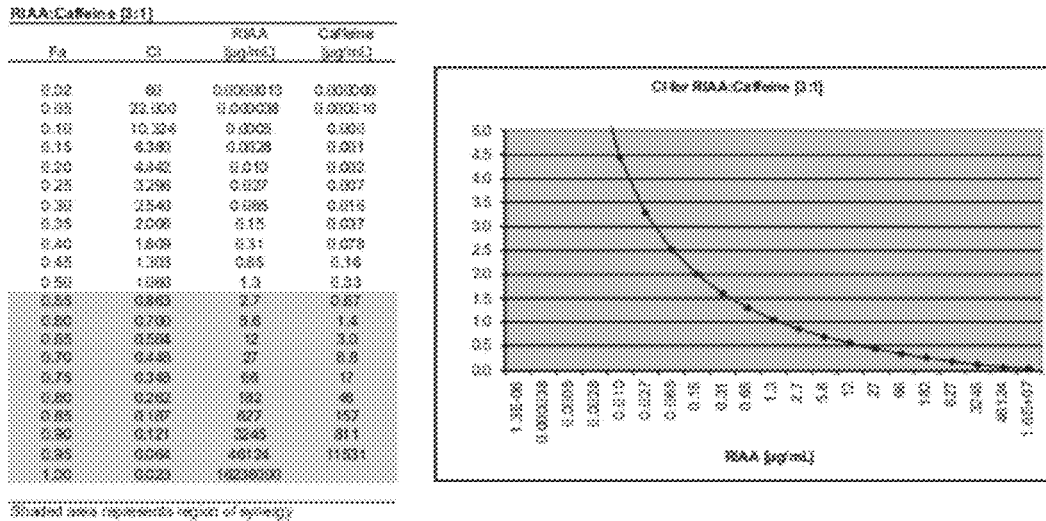
Figure 7D:
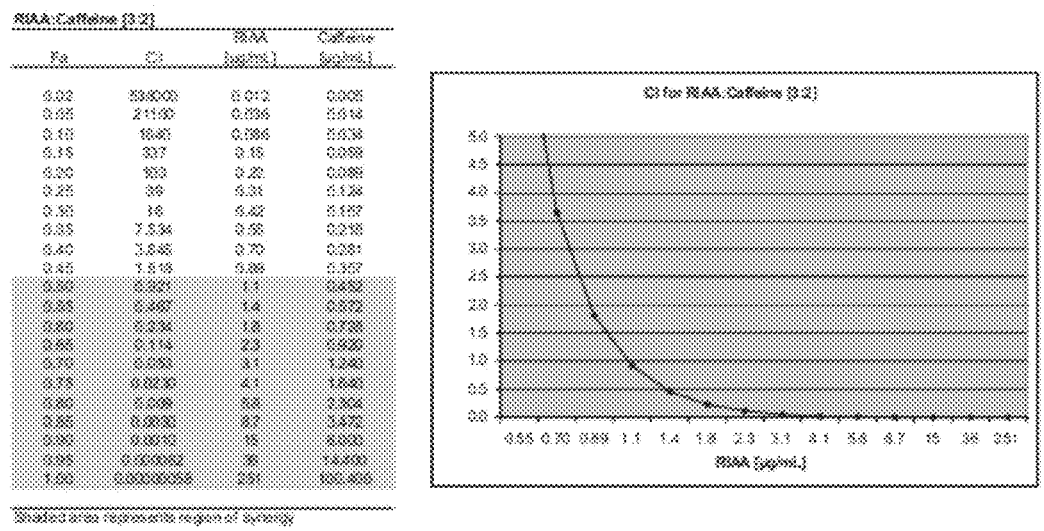
Figure 7G:
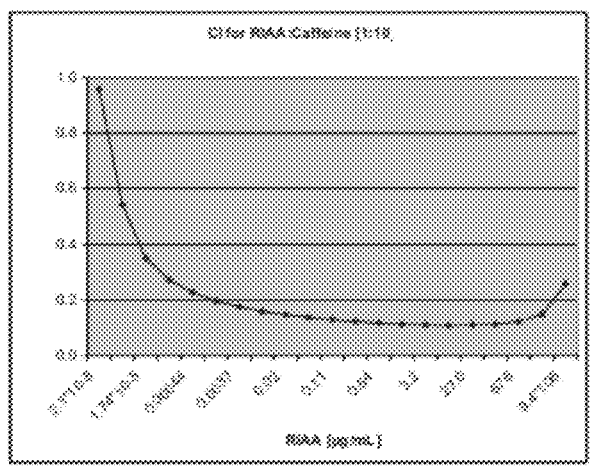
Figure 7H:
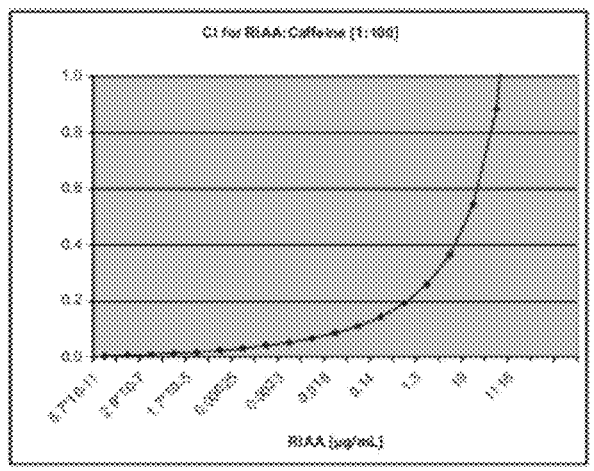

FIG. 7 shows a graphic representation of the computed Combination Index parameter versus the concentration of reduced isomerized alpha-acids (RIAA) for RIAA:caffeine ratios of 100:1 (FIG. 7A), 10:1 (FIG. 7B), 3:1 (FIG. 7C), 3:2, (FIG. 7D), 1:1 (FIG. 7E), 2:3 (FIG. 7F), 1:10 (FIG. 7G), 1:100 (FIG. 7H).

These results show that combinations of RIAA and caffeine from 100:1 to 1:100 RIAA:caffeine exhibited synergy in the inhibition of $PGE_2$ production in the LPS-stimulated RAW 267.4 model of inflammation at some portion of the dose-response curve. At concentrations of RIAA equal to or less than 60%, synergy was observed to be particularly effective.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A method of reducing inflammation, comprising administering to a subject in need thereof a composition comprising synergistic anti-inflammatory effective amounts of a compound selected from the group consisting of dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone and hexahydro-isoadhumulone, and a methylxanthine in a synergistic ratio having a combination index (CI) of less than 1.

2. The method of claim 1, wherein the compound is derived from hops.

3. The method of claim 1, wherein said compound is a member of Genus A having the formula:

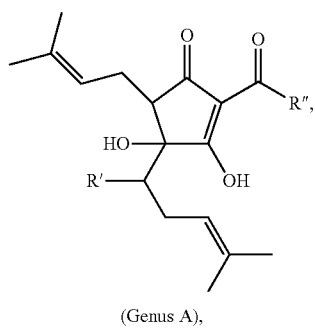

(Genus A), wherein R' is selected from the group consisting of carbonyl, hydroxyl, OR, and OCOR, wherein R is alkyl;

and wherein R" is selected from the group consisting of $CH(CH_3)_2$, $CH_2CH(CH_3)_2$, and $CH(CH_3)CH_2CH_3$.

4. The method of claim 1, wherein said methylxanthine is selected from caffeine; theobromine; theophylline; aminophylline; doxofylline; pentoxifylline; 8-oxopentoxifylline; 8-oxolisofylline; lisofylline; 1-proparagyl 3,7-dimethyl xanthine; 7-proparagyl 1,3-dimethyl xanthine; 3-proparagyl 1,7-dimethyl xanthine; 1,3,7-triproparagyl xanthine; 3-isobutyl-1-methylxanthine (IBMX); 1,3,7-tripropyl xanthine; 7-benzyl-IBMX; 1-propyl 3,7-dimethyl xanthine; 1,3-dipropyl 7-methyl xanthine; 1,3-dipropyl 7-proparagyl xanthine; 3,7-dimethyl 1-propyl xanthine; and 7-allyl 1,3-dimethyl xanthine.

5. The method of claim 1, wherein the methylxanthine is caffeine.

6. The method of claim 1, wherein the composition comprises about 50 to 7500 mg of the compound.

7. The method of claim 1, wherein the composition comprises about 0.001 to 10 weight percent of the compound.

8. The method of claim 1, wherein the composition comprises about 0.1 to 1 weight percent of the compound.

9. The method of claim 1, wherein the composition further comprises a pharmaceutically acceptable carrier.

10. The method of claim 1, wherein the composition is formulated for administration orally, topically, parenterally, or rectally.

11. The method of claim 1, wherein the compound and the methylxanthine are in a ratio of about 100:1 to about 1:100.

12. The method of claim 1, wherein the composition comprises about 0.5 to 10,000 mg of the compound.

13. A method of treating an inflammatory disease, comprising administering to a subject in need thereof a composition comprising synergistic anti-inflammatory effective amounts of a compound selected from the group consisting of dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone and hexahydro-isoadhumulone, and a methylxanthine in a synergistic ratio having a combination index (CI) of less than 1.

14. The method of claim 13, wherein the compound is derived from hops.

15. The method of claim 13, wherein said compound is a member of Genus A having the formula:

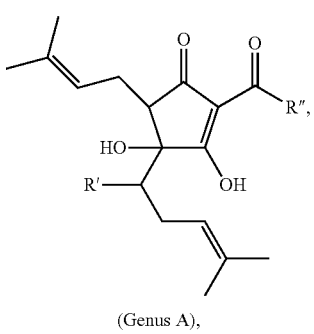

(Genus A), wherein R' is selected from the group consisting of carbonyl, hydroxyl, OR, and OCOR, wherein R is alkyl;

and wherein R" is selected from the group consisting of $CH(CH_3)_2$, $CH_2CH(CH_3)_2$, and $CH(CH_3)CH_2CH_3$.

16. The method of claim 13, wherein said methylxanthine is selected from caffeine; theobromine; theophylline; aminophylline; doxofylline; pentoxifylline; 8-oxopentoxifylline; 8-oxolisofylline; lisofylline; 1-proparagyl 3,7-dimethyl xanthine; 7-proparagyl 1,3-dimethyl xanthine; 3-proparagyl 1,7-dimethyl xanthine; 1,3,7-triproparagyl xanthine; 3-isobutyl-1-methylxanthine (IBMX); 1,3,7-tripropyl xanthine; 7-benzyl-IBMX; 1-propyl 3,7-dimethyl xanthine; 1,3-dipropyl 7-methyl xanthine; 1,3-dipropyl 7-proparagyl xanthine; 3,7-dimethyl 1-propyl xanthine; and 7-allyl 1,3-dimethyl xanthine.

17. The method of claim 16, wherein the methylxanthine is caffeine.

18. The method of claim 13, wherein the composition comprises about 50 to 7500 mg of the compound.

19. The method of claim 13, wherein the composition comprises about 0.001 to 10 weight percent of the compound.

20. The method of claim 13, wherein the composition comprises about 0.1 to 1 weight percent of the compound.

21. The method of claim 13, wherein the composition further comprises a pharmaceutically acceptable carrier.

22. The method of claim 13, wherein the composition is formulated for administration orally, topically, parenterally, or rectally.

23. The method of claim 13, wherein the compound and the methylxanthine are in a ratio of about 100:1 to about 1:100.

24. The method of claim 13, wherein the composition comprises about 0.5 to 10,000 mg of the compound.

25. The method of claim 13, wherein the inflammatory disease is selected from the group consisting of autoimmune disease, arthritis, rheumatoid arthritis, gouty arthritis, osteoarthritis, juvenile arthritis, menstrual cramps, tendonitis, bursitis, inflammatory bowel disease, Crohn's disease, gastritis, irritable bowel syndrome, ulcerative colitis, colorectal cancer, type I diabetes, and swelling after injury.

* * * * *